US008003599B2

(12) United States Patent
Altevogt et al.

(10) Patent No.: US 8,003,599 B2
(45) Date of Patent: Aug. 23, 2011

(54) INHIBITORS OF L1 AND ADAM10 FOR THE TREATMENT OF CARCINOMAS

(75) Inventors: Peter Altevogt, Neckargemünd (DE); Daniela Kelm, Dossenheim (DE); Mina Fogel, Gedera (IL)

(73) Assignee: Deutsches Krebsforschungszentrum, Heidelberg (DE)

( * ) Notice: Subject to any disclaimer, the term of this patent is extended or adjusted under 35 U.S.C. 154(b) by 807 days.

(21) Appl. No.: 11/573,269

(22) PCT Filed: Jul. 27, 2005

(86) PCT No.: PCT/EP2005/008148
§ 371 (c)(1),
(2), (4) Date: May 4, 2007

(87) PCT Pub. No.: WO2006/013051
PCT Pub. Date: Feb. 9, 2006

(65) Prior Publication Data
US 2008/0003222 A1    Jan. 3, 2008

(30) Foreign Application Priority Data
Aug. 6, 2004    (EP) .................................. 04018723

(51) Int. Cl.
*A61K 38/00*    (2006.01)
*C12N 15/11*    (2006.01)
(52) U.S. Cl. ...................................... 514/1.2; 514/44 A
(58) Field of Classification Search ............. 514/2, 44 A
See application file for complete search history.

(56) References Cited

U.S. PATENT DOCUMENTS

| 2003/0003449 A1* | 1/2003 | Menzel et al. | 435/6 |
| 2003/0211610 A1* | 11/2003 | Condon et al. | 435/375 |

FOREIGN PATENT DOCUMENTS

| WO | WO 02/04952 A2 | 1/2002 |
| WO | WO 03/051825 A1 | 6/2003 |
| WO | WO 03/106381 A2 | 12/2003 |
| WO | WO 2004037198 A2 * | 5/2004 |
| WO | WO 2004/089294 | 10/2004 |

OTHER PUBLICATIONS

Herskowitz (1987) Nature 329:219-222.*
International Search Report, PCT/EP2005/008148, Jul. 27, 2005.
Hoefnagel, C. A. e al., "A comparison of neuroblastoma with mIBG and anti L1-CAM antibody mAb chCE7: therapeutic efficacy in a neuroblastoma xenograft model and imaging of neuroblastoma patients", European Journal of Nuclear Medicine, Berlin, Germany, vol. 28, No, 3, Mar. 2001, pp. 359-368.
Mechtersheimer, Sabine et al., "Ectodomain shedding of L1 adhesion molecule promotes cell migration by autocrine biding to integrins", Journal of Cell Biology, vol. 155, No. 4, Nov. 22, 2001, pp. 661-673.

(Continued)

*Primary Examiner* — Jon E Angell
(74) *Attorney, Agent, or Firm* — Perkins Coie LLP; Viola T. Kung

(57) ABSTRACT

Described is a pharmaceutical composition comprising a compound(s) interfering with the biological activity of L1 and/or ADAM10 or their expression. Also described is the use of said compound(s) for the prevention/treatment of carcinomas like ovarian and endometrial carcinoma. Finally, the diagnosis of highly malignant forms of carcinomas which is based on the determination of the activity/expression of L1 and/or ADAM10 is described.

7 Claims, 20 Drawing Sheets

OTHER PUBLICATIONS

Fogel, M. et al., "L1 expression as a predictor of progression and survival in patients with uterine and ovarian carcinomas", Lancet The, Lancel Limited, London, GB, vol. 362, No. 9387, Sep. 13, 2003, pp. 869-875.

Hall, Ronelle J. and Erickson, Carol A., "ADAM10: an active metalloprotease expressed during avian epithelial morphogenesis", Developmental Biology, Apr. 1, 2003, vol. 256, No. 1, pp. 146-159.

Lammich, Sven et al., "Constitutive and regulated alpha-secretase cleavage of Alzheimer's amyloid precursor protein by a disintegrin metalloprotease", Proc. Natl. Acad. Sci. USA, vol. 96, No. 7, pp. 3922-3927, Mar. 1999.

Riedle, Svenja, "Untersuchungen zur ADAM10-vermittelten Spaltung von L1 in Ovarialkarzinomzellen" Dissertation, published Aug. 19, 2004 (with English translation of Abstract), English translation only part considered.

* cited by examiner

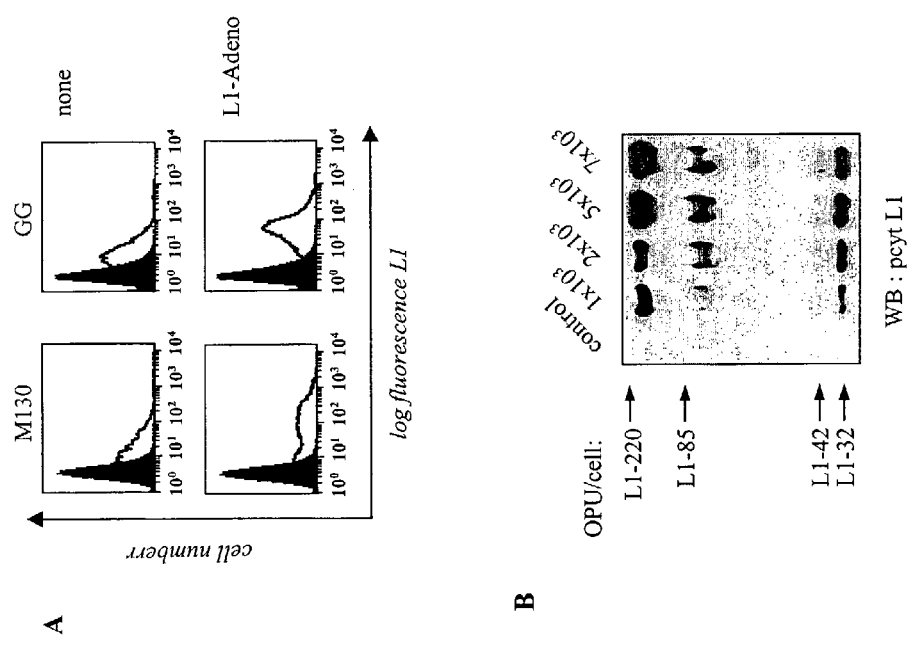

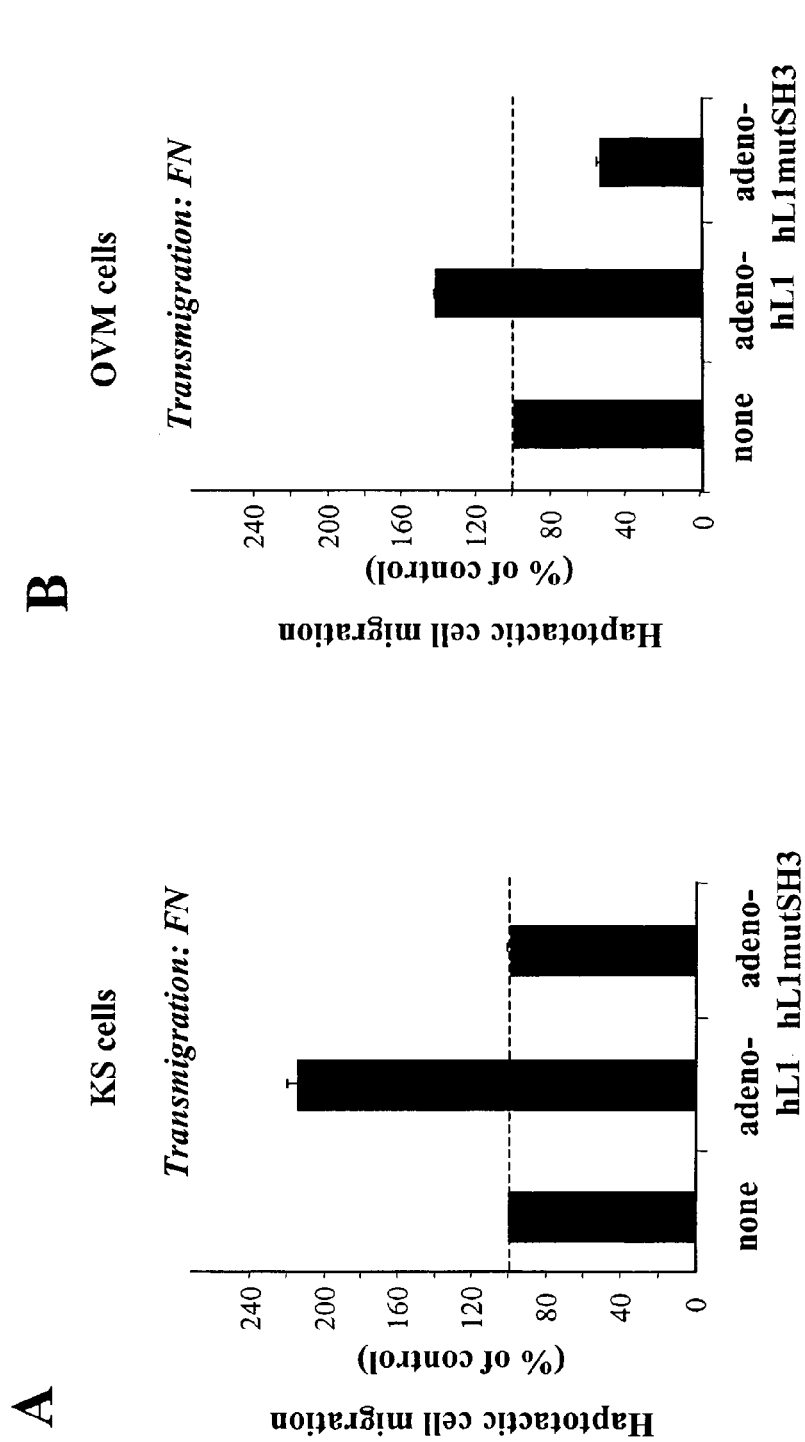

INHIBITORS OF L1 AND ADAM10 FOR THE TREATMENT OF CARCINOMAS

This application is a National Stage of International Application PCT/EP2005/008148, filed Jul. 27, 2005, published Feb. 9, 2006, under PCT Article 21(2) in English; which claims the priority of EP 04018723.9, filed Aug. 6, 2004.

REFERENCE TO SEQUENCE LISTING, TABLE OR COMPUTER PROGRAM

The Sequence Listing is submitted herewith the specification as an ASCII formatted text file via EFS-Web with a file name of Sequence_Listing.txt with a creation date of Jan. 10, 2011, and a size of 18.1 kilobytes. The Sequence Listing filed via EFS-Web is part of the specification and is hereby incorporated in its entirety by reference herein.

The present invention is based on the observation that L1 and ADAM10 are overexpressed in highly malignant carcinomas. Thus, the present invention relates to a pharmaceutical composition comprising (a) compound(s) interfering with the biological activity of L1 and/or ADAM10 or their expression. The present invention also relates to the use of said compounds for the prevention/treatment of carcinomas like ovarian and endometrial carcinoma. Finally, the present invention also relates to the diagnosis of highly malignant forms of carcinomas which is based on the determination of the activity/expression of L1 and/or ADAM10.

The ability of primary tumor cells to disseminate and form tumor metastasis is associated with profound changes in cellular properties among which the acquisition of migratory and proteolytic ability are considered most important. Ovarian and highly aggressive endometrial carcinomas are the most common cause of cancer related deaths among gynecological malignancies. The serous papillary subtype of these tumors is associated with extensive metastatic spread within the abdominal cavity leading to an advanced stage at presentation and a poor prognosis for the patient. After the formation of peritoneal tumor implants, tumor cells invade beneath the mesothelial layer into the underlying extracellular matrix and frequently metastasize through the lymphatics to distant organs.

Tumor cells can re-express adhesion molecules involved in cell adhesion and migration during tissue morphogenesis and fetal development that are silenced under non-malignant conditions. Such ectopically expressed molecules may contribute to tumor dissemination. The L1 adhesion molecule is a 200-220 kD type I membrane glycoprotein of the immunoglobulin super family (IgSF), consisting of 6 Ig-like domains and five fibronectin-type III repeats followed by a transmembrane region and a highly conserved cytoplasmic tail. In neuronal cells, L1 is involved in morphogenic events, such as neuron-neuron adhesion, neurite fasciculation, synaptogenesis, neurite outgrowth on Schwann cells and neuronal cell migration. L1 is also involved in the branching of renal tubes in the kidney. In humans, mutations in the L1 gene cause abnormal brain development, characterized by mental retardation and defects in central nervous system axon tracts such as the corpus callosum and corticospinal tract. Absence of L1 in knockout mice has given evidence that the molecule is critical in brain development in different brain regions.

L1 is also expressed by hematopoietic and certain epithelial cells as well as by a variety of tumor cell lines (Kowitz et al., Clin. Exp. Metastasis 11(5) (1993), 419-29; Ebeling al., Eur. J. Immunol. 26(10) (1996), 2508-16; Pancook et al., J. Immunol. 158(9), 4413-21); Fogel et al., Cancer Lett. 189(2) (2003), 237-47). Recently, it was reported that L1 is strongly expressed in ovarian and aggressive uterine carcinomas in situ whereas the normal epithelial counter tissues were negative (Fogel et al., Lancet 362(9387) (2003), 869-75). In a retrospective study, L1 was found in 46/58 ovarian carcinomas. L1 negative tumors had a good prognosis but L1 expression indicated short survival for the patient. Amongst the 72 patients with uterine adenocarcinomas 20 patients were positive for L1. Strikingly, patients with L1 positive uterine tumors were at high risk for progression even in the endometrioid-type tumors that usually have a favourable prognosis. Thus, L1 expression identified the highly aggressive forms of ovarian and uterine tumors. However, the underlying mechanism why L1 positive tumors are endowed with higher malignant potential remained unknown. Unfortunately, so far no approaches to replace unspecific therapies by a specific treatment of such malignancies were available. The current protocols use chemotherapy with, e.g., cis-Platin or taxol for ovarian and endometrial carcinomas which often results in therapy resistance. There are no drugs available that can break the resistance.

Thus, the technical problem underlying the present invention is to provide means suitable for treating or preventing carcinomas, preferably highly malignant forms of carcinomas, which avoid the induction of resistance.

The solution of the said technical problem is achieved by providing the embodiments characterized in the claims.

Ovarian epithelial tumors disseminate by the formation of peritoneal tumor implants through the abdominal cavity and invasion beneath the mesothelial layer into the underlying extracellular matrix. Cell adhesion and migration are critical steps during this process. The L1 adhesion molecule, an important mediator for cell adhesion and migration in neural cells, is overexpressed in ovarian and endometrial tumors. In the experiments leading to the present invention it could be shown that L1 supports the binding of ovarian tumor cells to peritoneal mesothelial cells that could be specifically blocked with anti-L1 antibodies or L1-Fc fusion protein. The soluble ectodomain of L1 could be purified from the ascites of ovarian tumor patients. Overexpression of L1 by adenovirus mediated gene transfer or the addition of soluble L1 enhanced haptotactic cell migration on extracellular matrix proteins. L1 cleavage required the membrane-bound metalloproteinase ADAM10, that is expressed in ovarian carcinoma cell lines and tumor tissues. A method is described to block the motile phenotype of ovarian and endometrial carcinomas by using functional interference with L1 and ADAM10. For L1 the functional interference was achieved by expression (either via transfection or viral gene delivery systems) of a mutant form of L1 that has been rendered inactive by site directed mutagenesis of two amino acids (T1247A, S1248A positions according to neural L1). For ADAM10, functional interference was achieved by using a dominant negative form that has been mutated in the catalytic domain (E384A). Expression of the two mutant proteins abrogates the migration of ovarian carcinoma cells on various extracellular matrix proteins (Fibronectin, Laminin) in transmigration assays. The inactivation of two functionally important proteins is expected to be therapeutically usefully to prevent the growth and dissemination of carcinomas, e.g., ovarian and endometrial carcinomas. Thus, improved treatment of carcinoma, in particular ovarian and endometrial carcinoma, can be achieved by suppressing tumor migration and tumor progression via interference with ADAM10 and L1 function. In other words, the new strategy based on the findings of the present invention functionally inactivates the L1 adhesion molecule and the protease ADAM10 that are overexpressed in highly malignant forms of carcinomas like ovarian and endometrial carcinomas. The targeted downregulation of these antigens or their functional inactivation represents a novel concept and is distinctly different from the present treatment modalities.

(B) Detection of L1 and ADAM10 in serial tissue sections of paraffin embedded ovarian carcinomas by histochemical staining using mAbs L1-11A and #2547. Examples from three individual carcinomas are shown.

Figure 2:
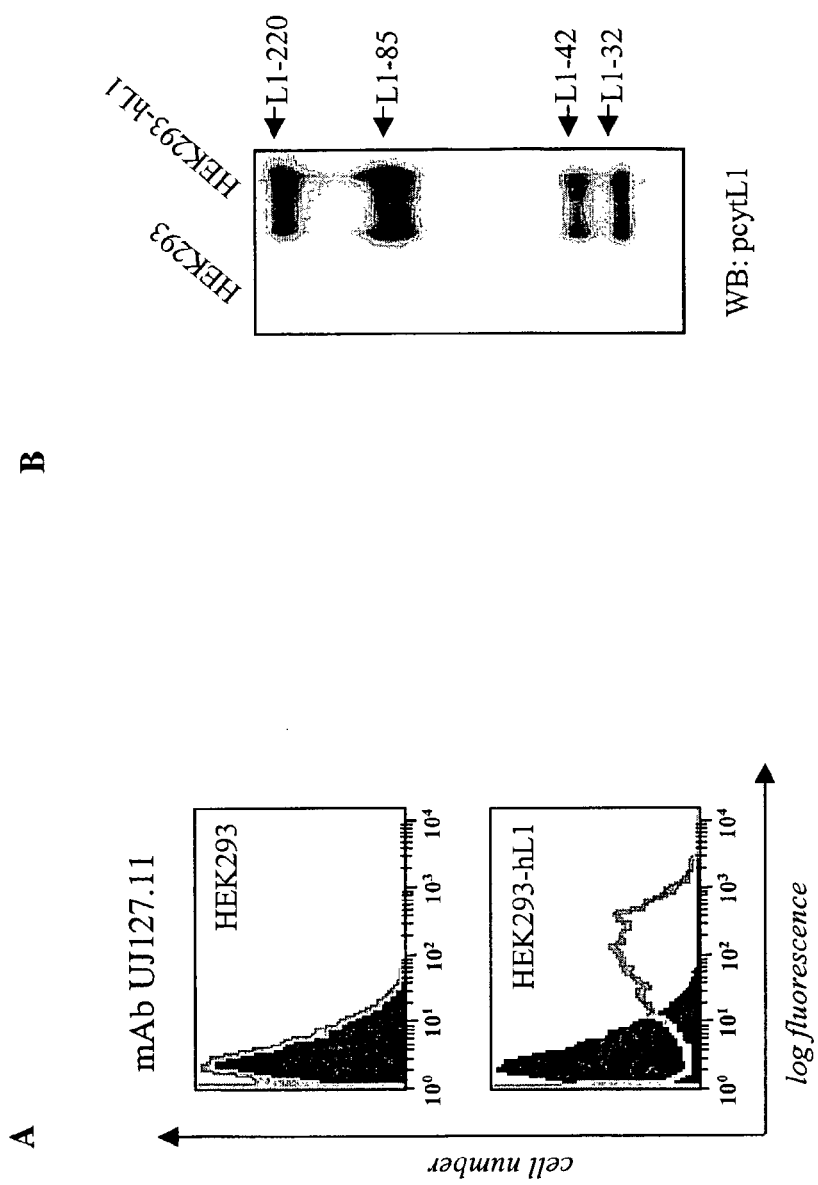
Figure 2:
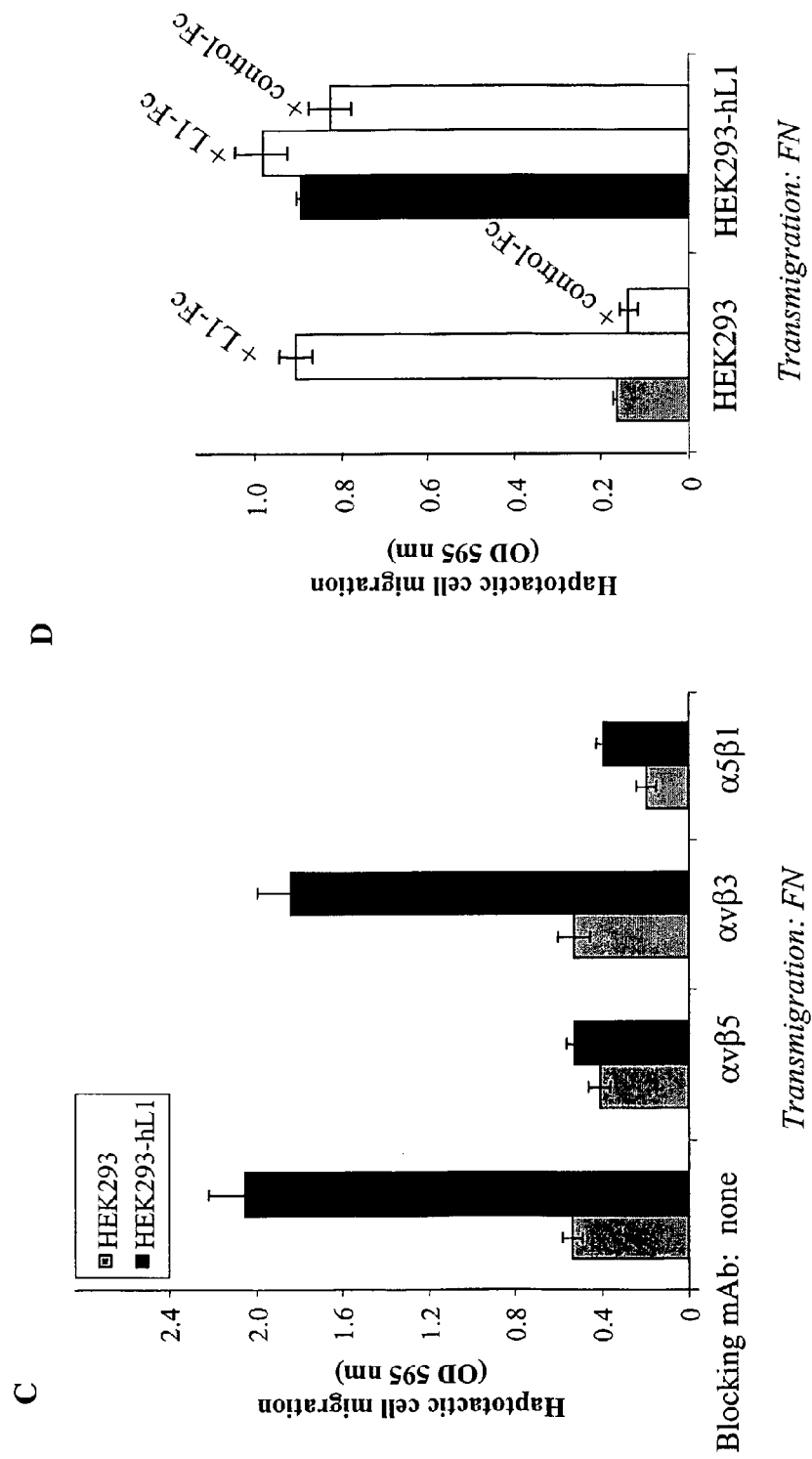

FIG. 2: Overexpression of L1 in HEK293 cells augments haptotactic cell migration (A) FACS analysis of stably transfected HEK293-hL1 cells using mAb L1-11A to L1 followed by PE conjugated anti mouse IgG.

(B) Western blot analysis of cell lysates of HEK293 and HEK293-hL1 cells. The cell pellet was lysed and analysed by Western blot with pcytL1 recognizing the cytoplasmic portion of L1 followed by peroxidase-conjugated secondary antibody and ECL detection. For L1 cleavage fragments see Gutwein et al., Faseb J. 17 (2003) 292-4.

(C) Inhibition of haptotactic cell migration in the absence or presence of the indicated mAbs to integrins at a final concentration of 10 µg/ml. FN at 10 µg/ml or BSA for control were coated onto the backside of Transwell chambers. Cells were seeded into the top chamber and allowed to transmigrate for 16 hr at 37° C. The antibody was present during the assay time. Each determination was done in quadruplicate and transmigrated cells were stained from the back of the filter. The dye was eluted from the filter and measured at 595 nm. The amount of dye is proportional to the number of transmigrated cells. Values for the migration on BSA were below 0.25 O.D. units for each cell type.

(D) Stimulation of cell migration by recombinant L1-Fc. The fusion protein and human IgG1 for control was added at the final concentration of 0.6 µg/ml. Migration was measured as described above.

Figure 3:
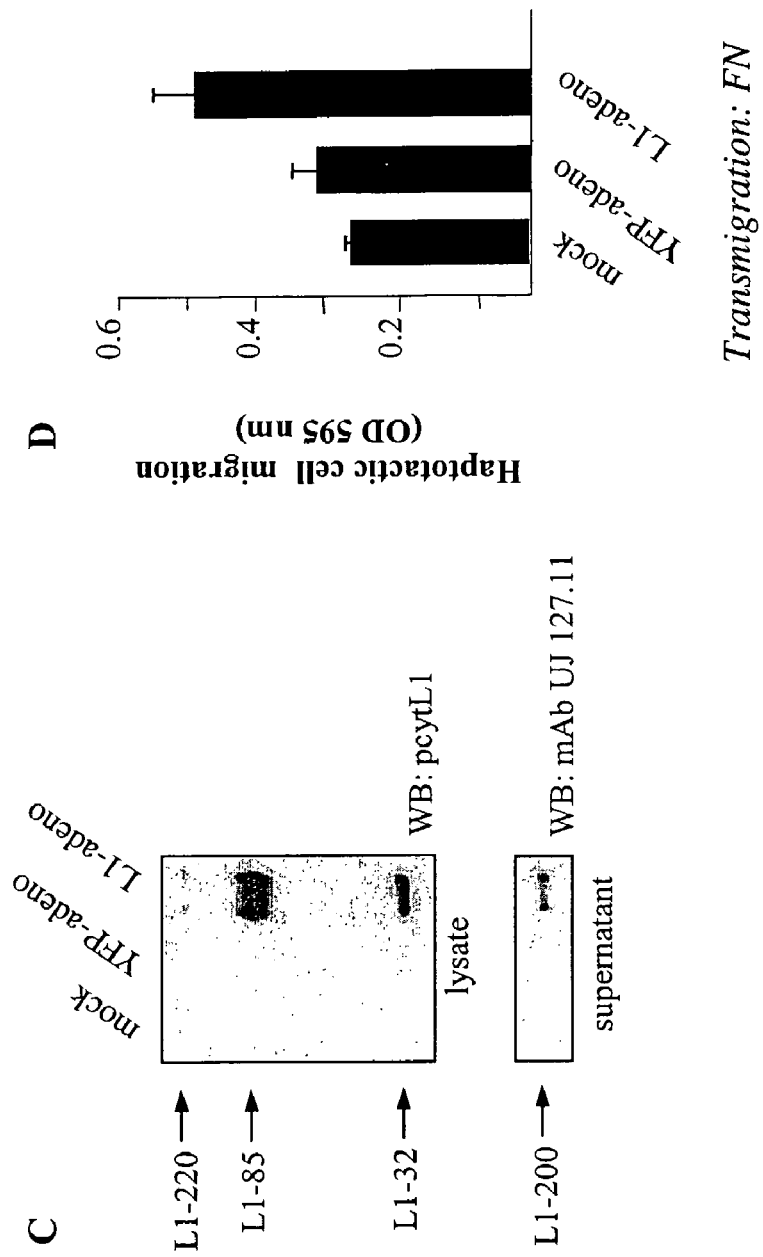
Figure 3:
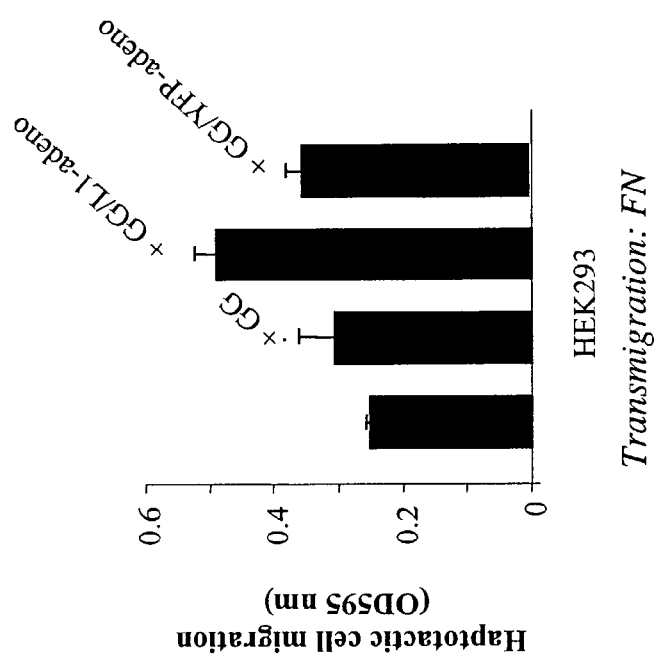

FIG. 3: Overexpression of L1 affects cleavage and migration (A) Infection of ovarian carcinoma cells M130 and GG with L1-adenovirus augments L1 cell surface expression. Cells were stained with mAb UJ 127.11 to the ectodomain of L1 followed by PE-conjugated anti-mouse IgG and analysed by FACS.

(B) Infection of GG cells with L1-adenovirus augments L1 expression in cell lysate. L1 were detected by pcytL1 followed by peroxidase-conjugated secondary antibody and ECL detection. For L1 cleavage fragments see Gutwein et al., supra.

(C) GG cells were infected with the indicated adenoviral vectors and 48 h after infection the cell lysate and the cell supernatant were analysed for the presence of L1.

(D) GG cells were infected with the indicated adenoviral vectors and 48 h after infection the haptocatic cell migration on fibronectin was examined.

(E) Conditioned medium of infected GG cells was concentrated tenfold and used to stimulate haptotactic cell migration of HEK293 cells. The migration assays were carried out as described in the legend of FIG. 2.

Figure 4:
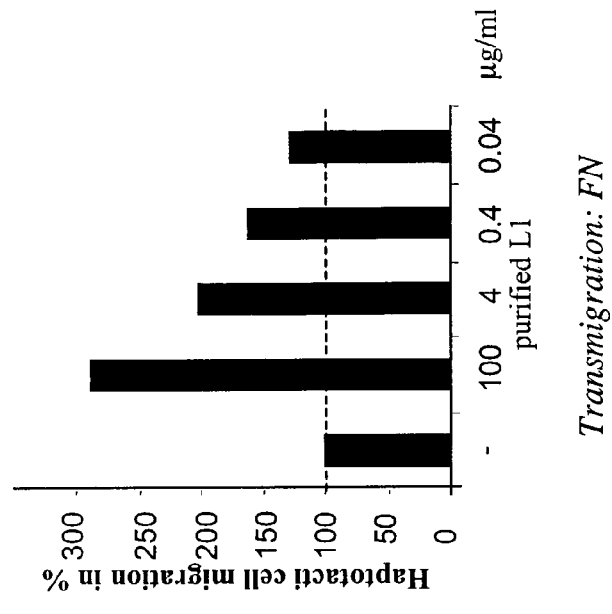
Figure 4:
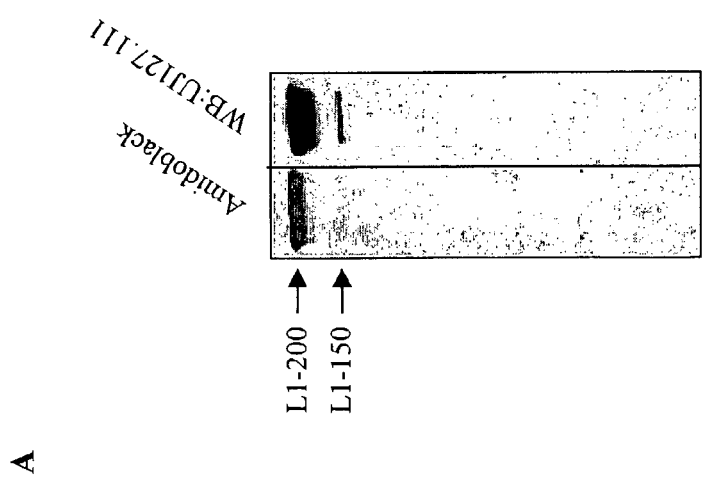
Figure 4:
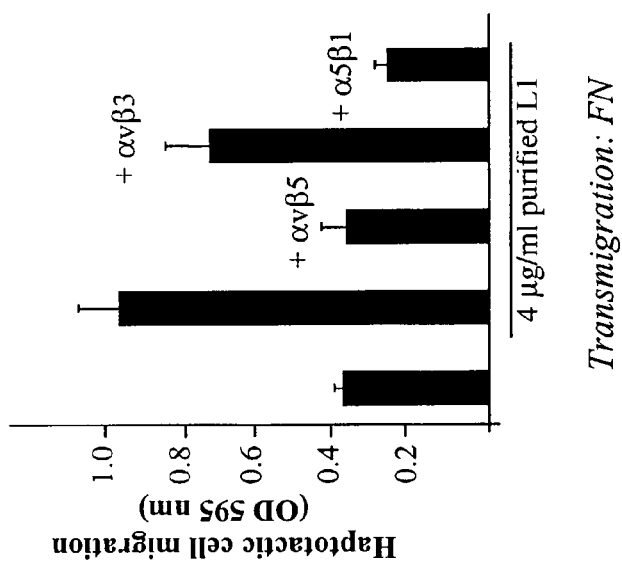

FIG. 4: Analysis of soluble L1 in the ascites fluid of tumor patients (A) Purification of soluble L1 from the ascites fluids of ovarian carcinoma patients by affinity chromatography using L1-11A Sepharose. An aliquot of purified L1 was separated by SDS-PAGE. The membrane was stained with amidoblack to visualize protein and then L1 was detected by mAb L1-11A followed by peroxidase-conjugated secondary antibody and ECL detection.

(B) Purified L1 stimulates cell migration. Soluble L1 at the indicated concentration was added to HEK293 cells and haptotactic migration on FN was examined as described in the legend to FIG. 2.

(C) HEK293 cells stimulated with soluble L1 were preincubated with the indicated mAbs at 10 pg/ml and haptotactic migration on FN was examined. The mAbs were present during the assay time. The assay was performed as described in the legend to FIG. 3.

Figure 5:
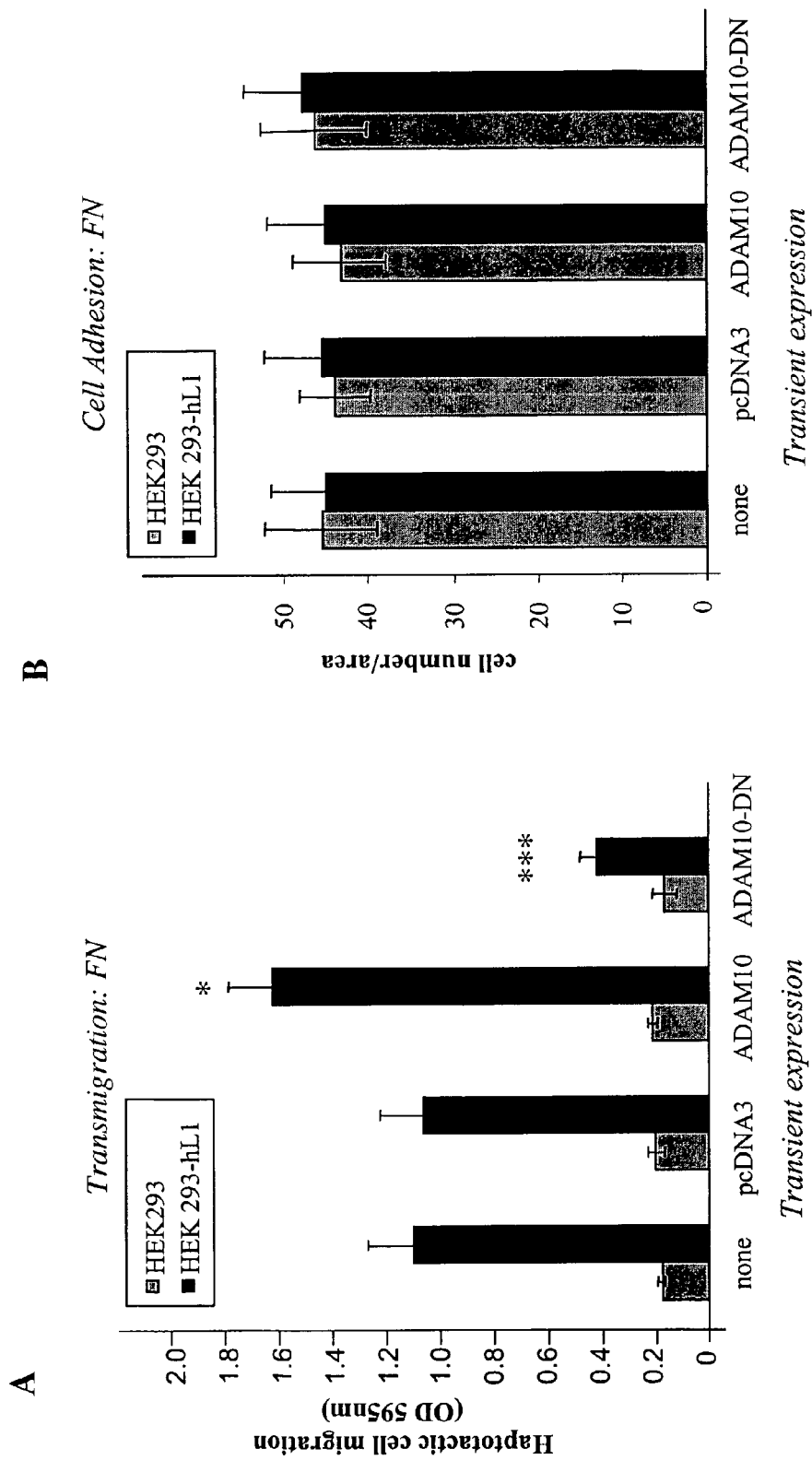

FIG. 5: An essential role of ADAM10 in L1-enhanced cell migration HEK293 cells and HEK293-hL1 cells were transiently transfected with plasmids (10 µg DNA) encoding ADAM10, ADAM10-DN or empty pcDNA3 vector using calcium phosphate. Control transfection with YFP-plasmid showed >50% transfection efficacy. 24 h after transfection cells were analysed.

(A) Haptotactic cell migration on fibronectin as substrate. Each determination was done in quadruplicate and transmigrated cells were stained from the backside of the filter as described in FIG. 2.

(B) Analysis of cell adhesion. FN or BSA for control were coated on LABTEK chamber slides and the adhesion of cells and transfectants were determined in the presence of 2 mM $Ca^{2+}$ and 2 mM $Mg^{2+}$. Binding to BSA was below 5 cells/area. *p=0.029; comparing ADAM10 transfected versus none-transfected cells; ***p=0.029 comparing ADAM10-DN versus none-transfected cells.

Figure 6:
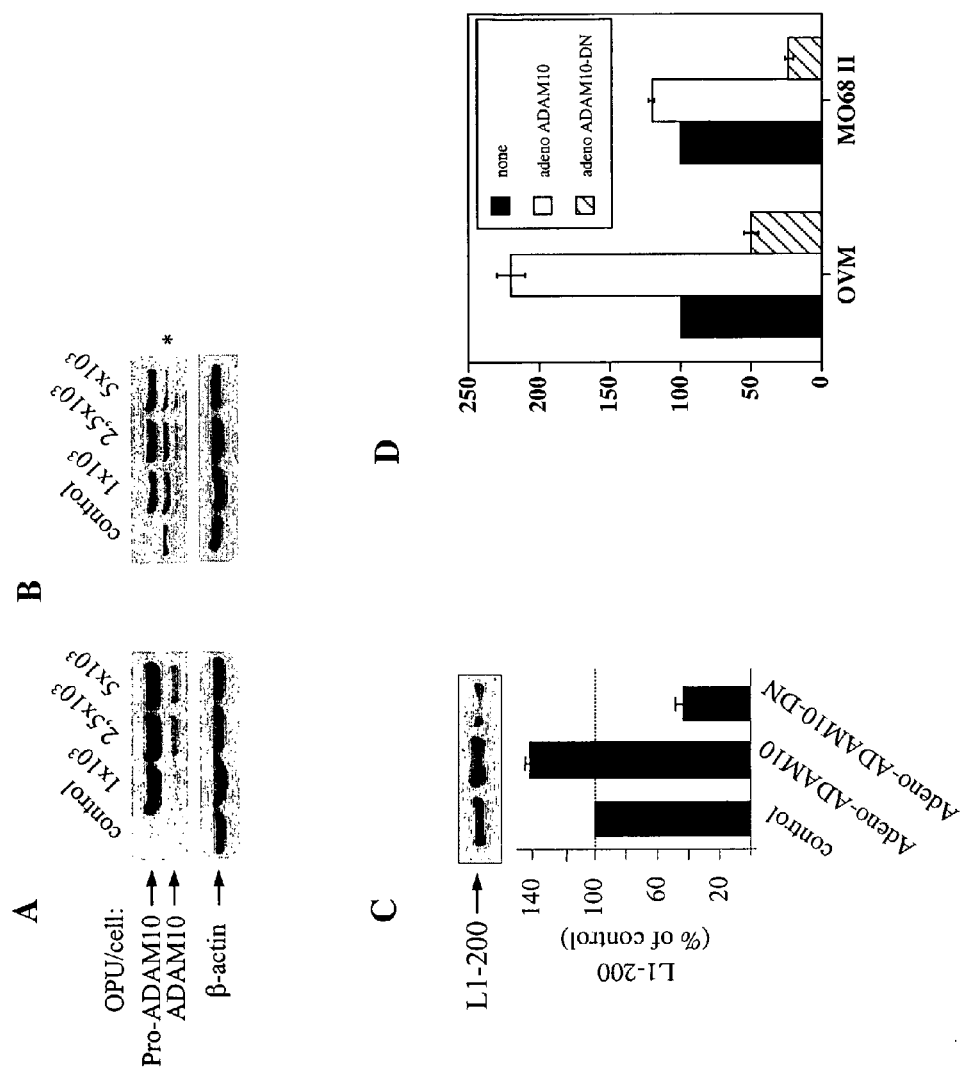

FIG. 6: Overexpression of dominant-negative ADAM10 blocks migration of ovarian carcinomas (A and B) Construction of HA-tagged adeno-ADAM10 and FLAG-tagged ADAM10-DN. OVMz cells were infected with the indicated recombinant adenovirus. Cells were lysed 24 hr later and lysates were probed with mAb to the HA-tag or FLAG-tag. * the indicated band is non-specific. (B) Infected OVMz cells were cultivated for 48 hr and analysed for L1 shedding. The supernatants were probed for the presence of soluble L1 by Western blotting using mAb L1-11A followed by peroxidase-conjugated secondary antibody and ECL detection. (C) OVMz and MO68 II cells were infected with the indicated adenovirus vectors and 48 h after infection the cells were analysed for haptotactic cell migration on fibronectin as substrate. The experiments were done three times with similar results. A representative study is shown.

Figure 7:
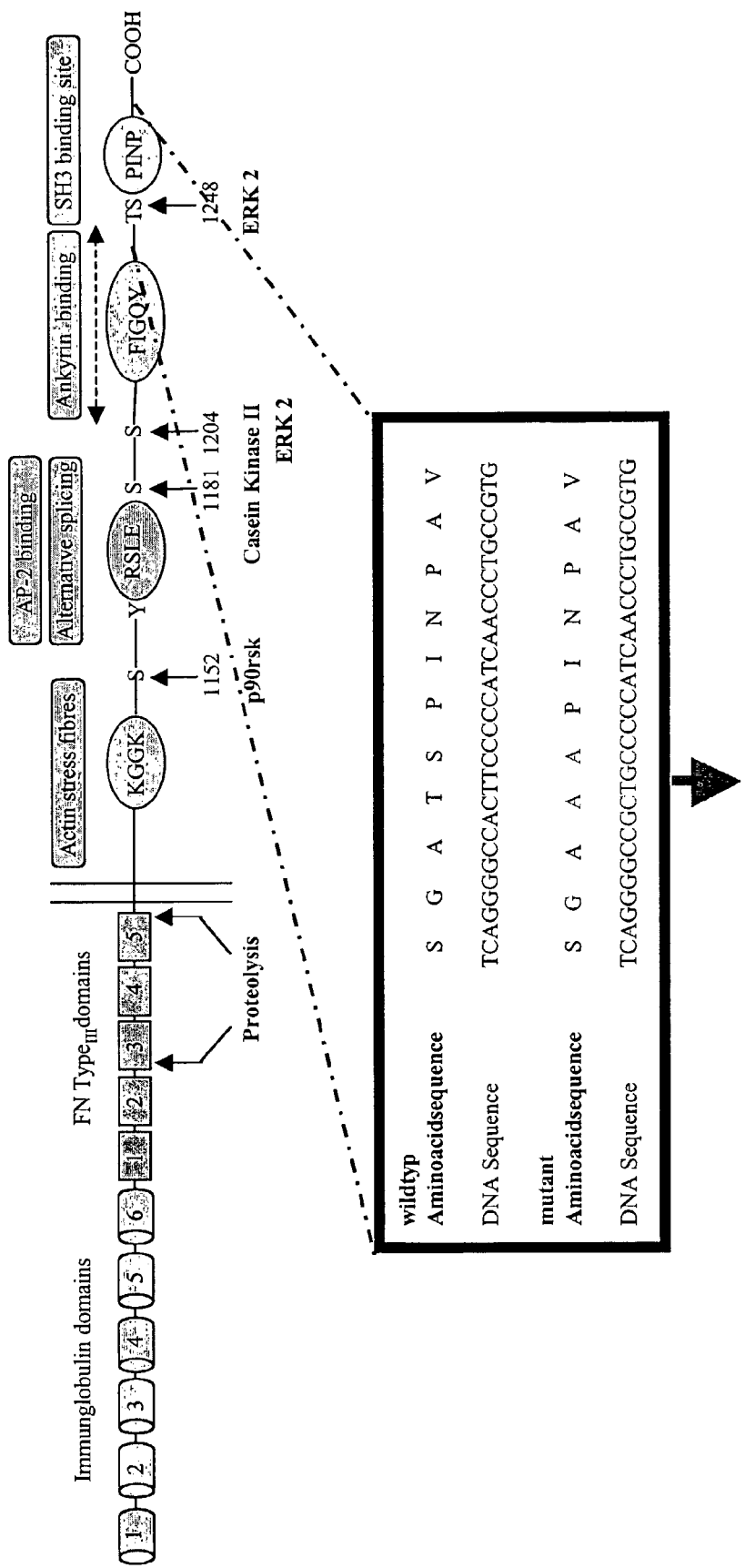

FIG. 7: Production of a mutant L1 form

A schematic view of the intracellular part of L1. Amino cid motifs and putatve interaction sites for kinases or binding sites for cytosceletal proteins are indicated. The putative SH3 binding site TSPINP (SEQ ID NO: 7) is also shown and the changes introduced by site directed mutagenesis to create the L1mutIII mutant form are boxed. SEQ ID NO: 3 is the wild type DNA sequence of FIG. 7. SEQ ID NO: 4 is the wild type protein sequence of FIG. 7. SEQ ID NO: 5 is the mutant DNA sequence of FIG. 7. SEQ ID NO: 6 is the mutant protein sequence of FIG. 7.

Figure 8:
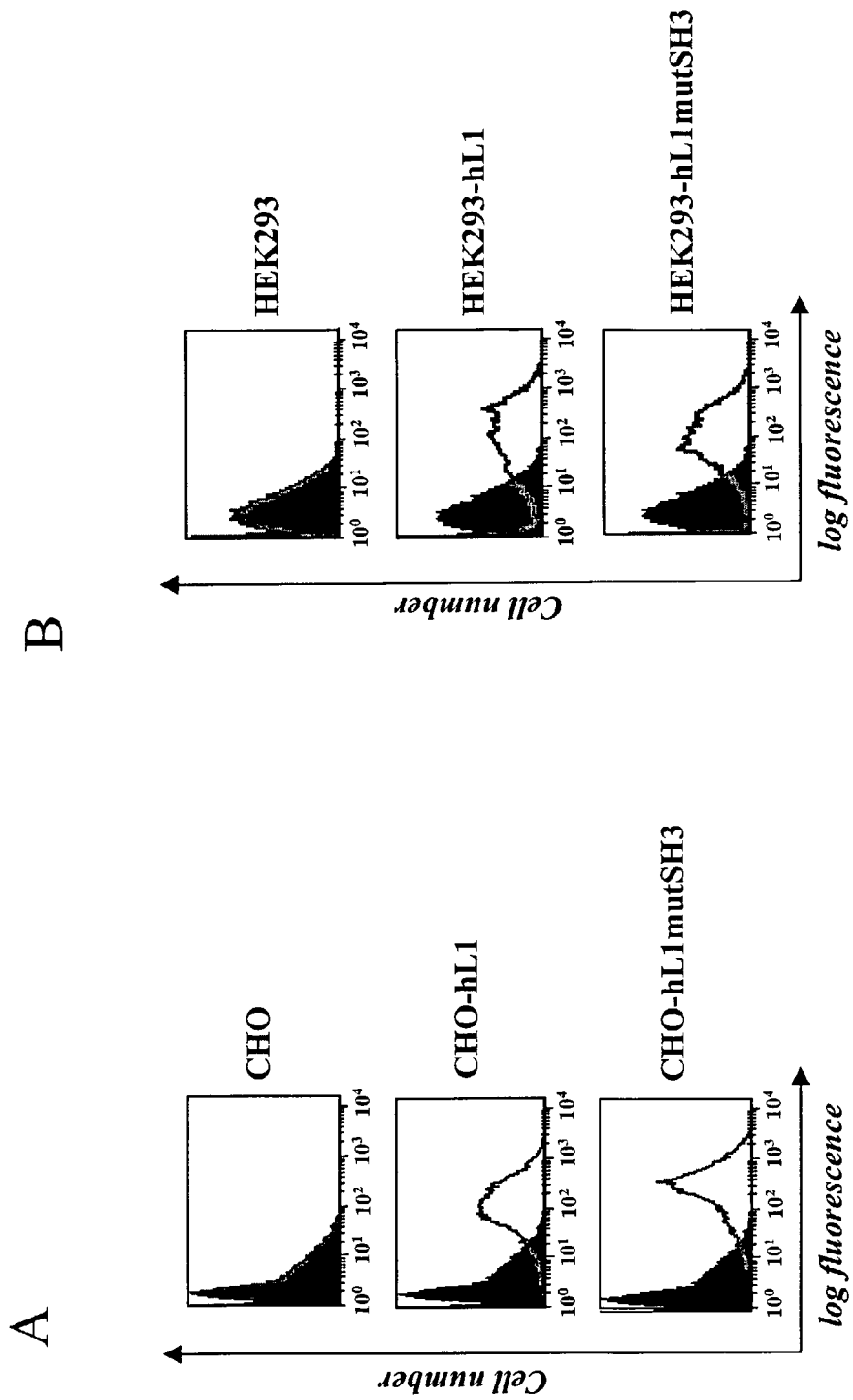
Figure 8:
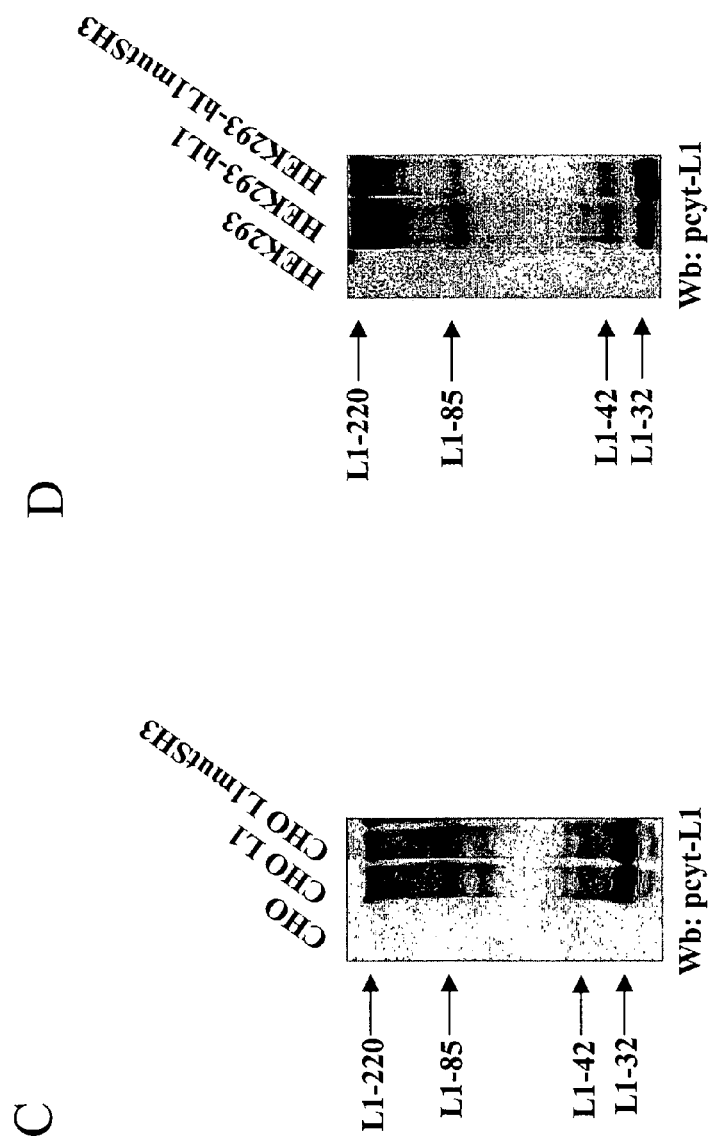

FIG. 8: Biochemical charcterization of stable cell lines expressing wildtype and matant L1.

FACS analysis of stably transfected CHO cells (A) or HEK293-hL1 cells (B) expressing the indicted wildtpye L1

L1mutSH3 forms. Cells were stained with mAb L1-11A to L1 followed by PE conjugated anti mouse IgG. Western blot analysis of transfected CHO cells (C) or HEK293-hL1 cells (D). The cell pellet was lysed and analysed by Western blot with pcytL1 recognizing the cytoplasmic portion of L1 followed by peroxidase-conjugated secondary antibody and ECL detection. For L1 cleavage fragments see Gutwein et al., Faseb J. 17 (2003), 292-294.

Figure 9:
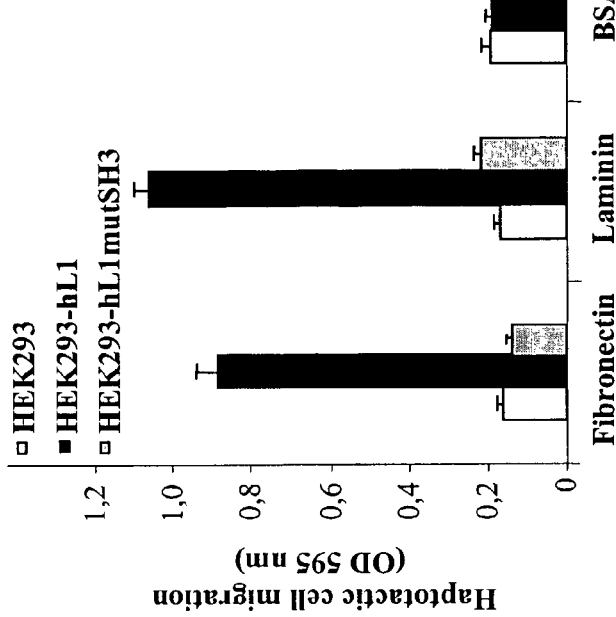
Figure 9:
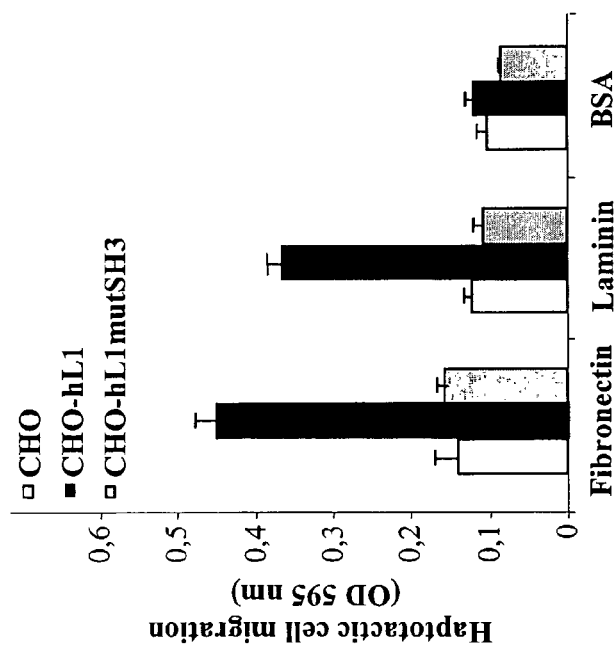

FIG. 9: Impaired cell migration of cells expressing a mutant form of L1

Analysis of haptotactic cell migration. FN and laminin at 10 μg/ml or BSA for control were coated onto the backside of Transwell chambers. (A) stably tranfected CHO cells and (B) HEK293 cells were seeded into the top chamber and allowed to transmigrate for 16 hr at 37° C. Each determination was done in quadruplicate and transmigrated cells were stained from the back of the filter. The dye was eluted from the filter and measured at 595 nm. The amount of dye is proportional to the number of transmigrated cells. Values for the migration on BSA were below 0.25 O.D. units for each cell type.

Figure 10:
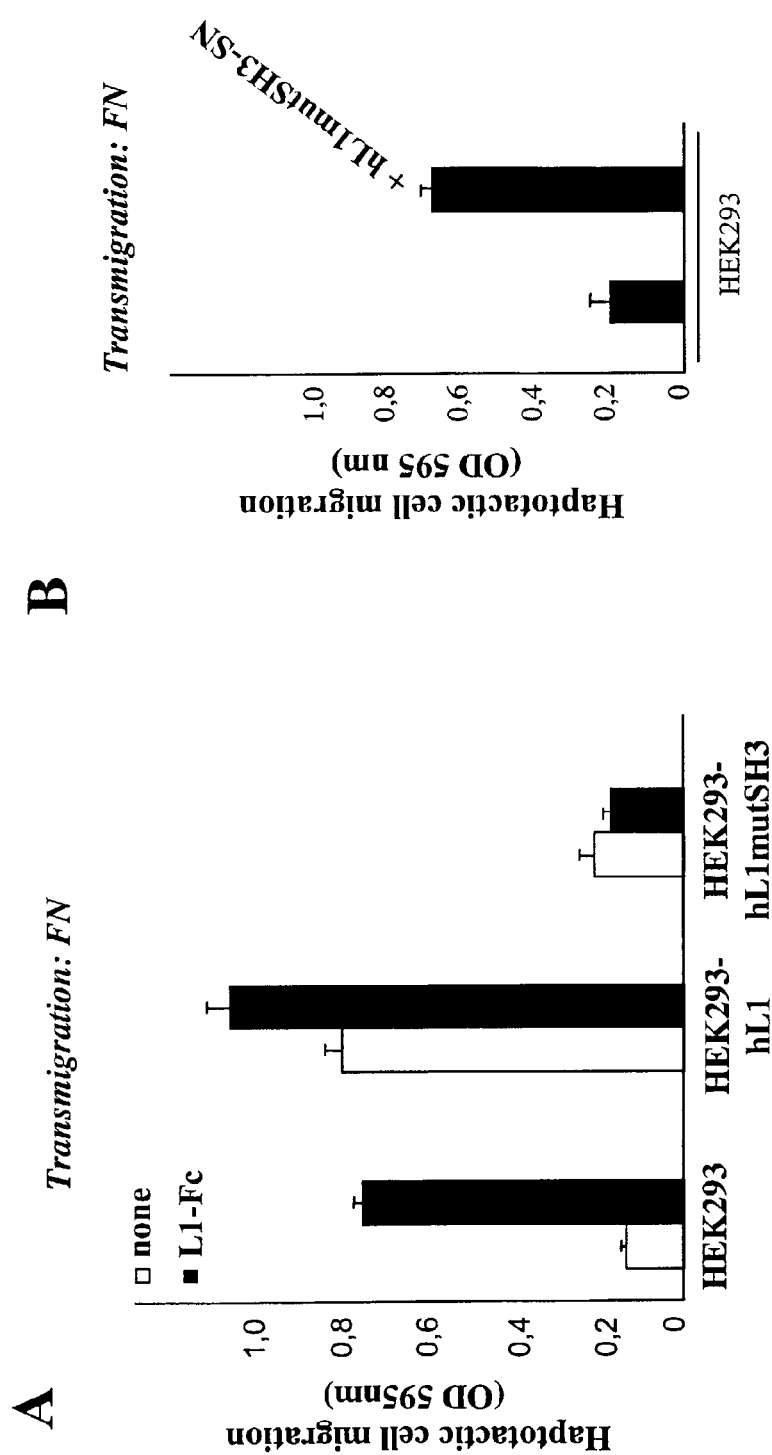

FIG. 10: Analysis of soluble L1 to stimulate L1mutSR3-HEK293 cells (A) Stimulation of cell migration by recombinant L1-Fc. The fusion protein was added at the final concentration of 0.6 pg/ml. Migration was measured as described above. (B)

Stimulation of cell migration by L1mutSH3-HEK293 supernatant. Conditioned medium was concentrated tenfold and used to stimulate haptotactic cell migration of HEK293 cells. The migration assays were carried out as described above.

Figure 11:
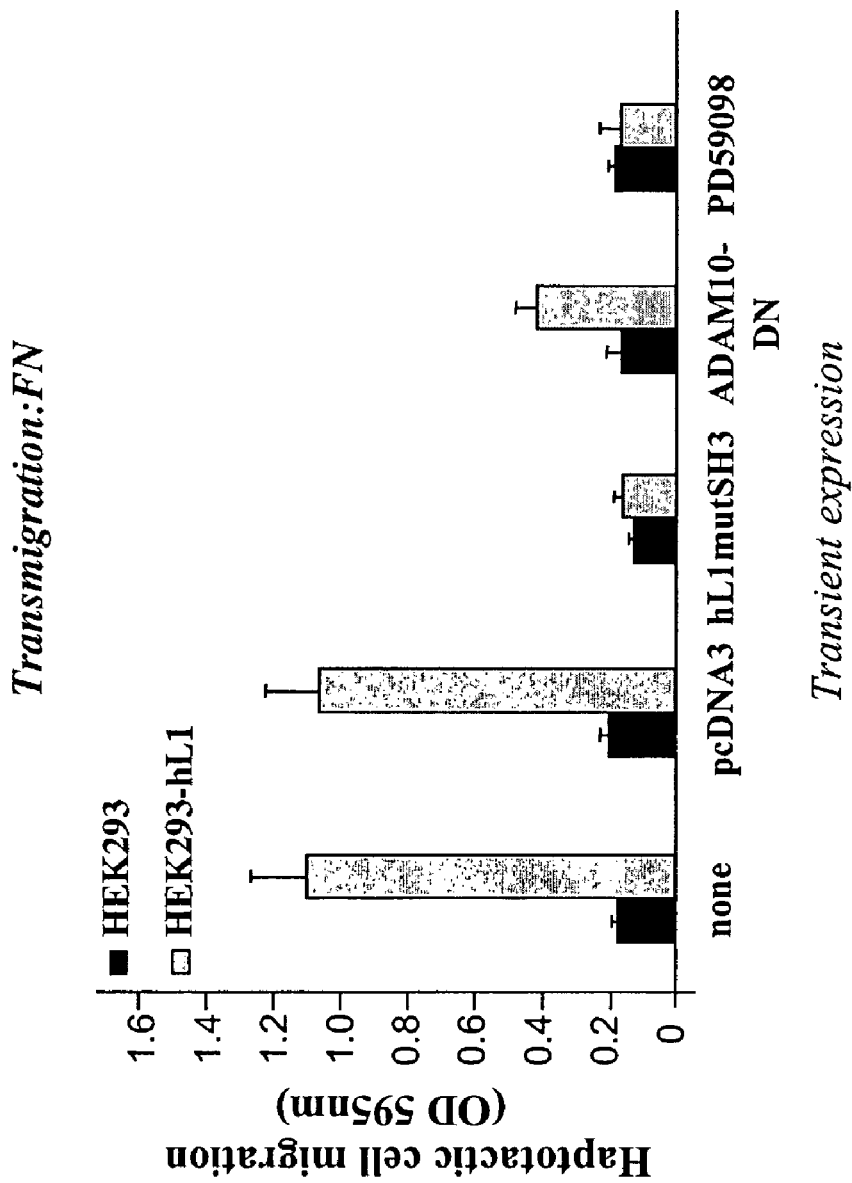

FIG. 11 Transient expression of mutant L1mutSR3 or a dominant-negative form of ADAM10 can suppress cell migration HEK293 cells and HEK293-hL1 cells were transiently transfected with plasmids (10 pg DNA) encoding hL1mutSH3, ADAM10-DN or empty pcDNA3 vector using calcium phosphate. Control transfection with YFP-plasmid showed >50% transfection efficacy. 24 h after transfection cells were analysed for haptotactic cell migration on fibronectin as substrate. Each determination was done in quadruplicate and transmigrated cells were stained from the backside of the filter. The MAP kinase specific inhibitor PD59098 could block the L1-dependent migration. The migration assays were carried out as described in the legend to FIG. 9.

Figure 12:
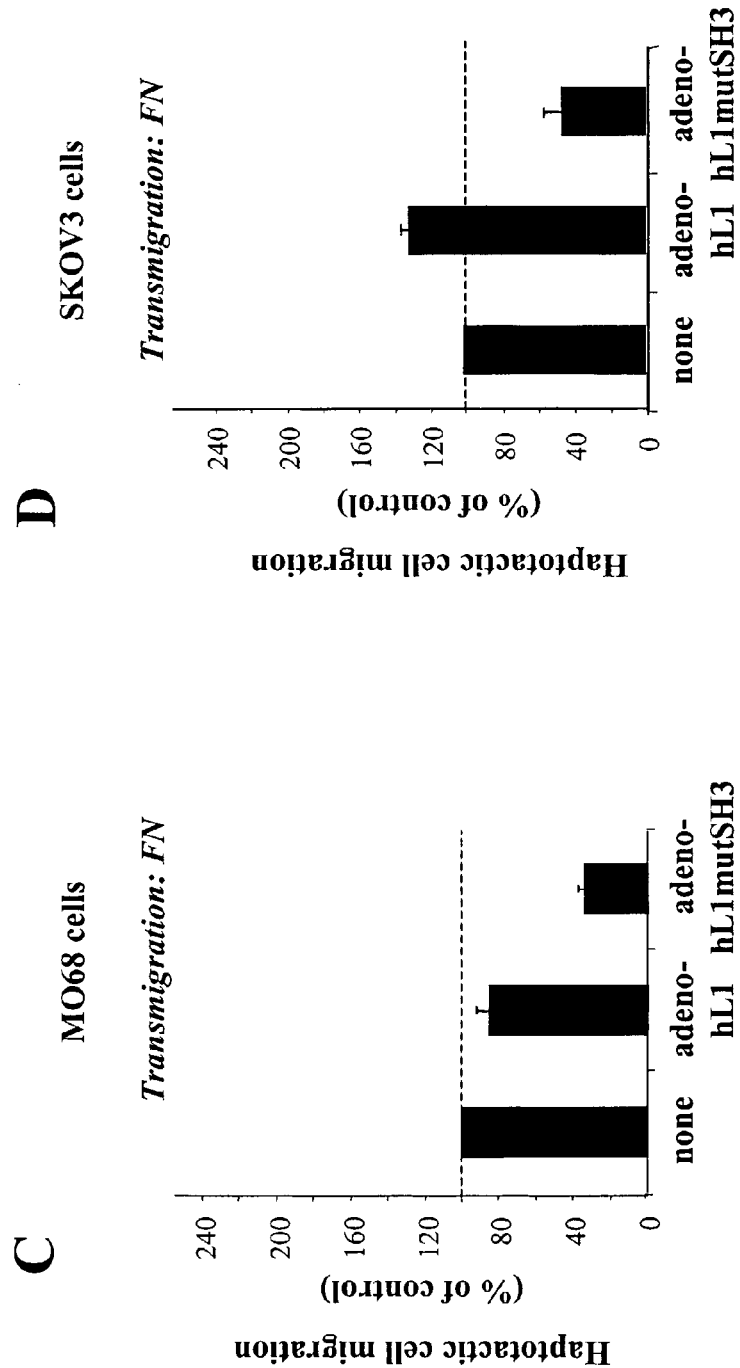

FIG. 12: L1-dependent migration of carcinoma cells is suppressed by adenoviral mutant hL1mutSH3

(A) Infection of L1 negative breast carcinoma cells KS with L1-adenovirus augments L1-dependent migration. Infection with adeno hL1mutSH3 has no effect. (B,C,D) Infection of L1 positve ovarian carcinoma cells OVM, MO68 and SKOV3 with L1-adenovirus augments L1-dependent migration. In contrast, infection with adeno hL1mutSH3 has a suppressive effect. The migration assays were carried out as described in the legend to FIG. 9.

Figure 13:
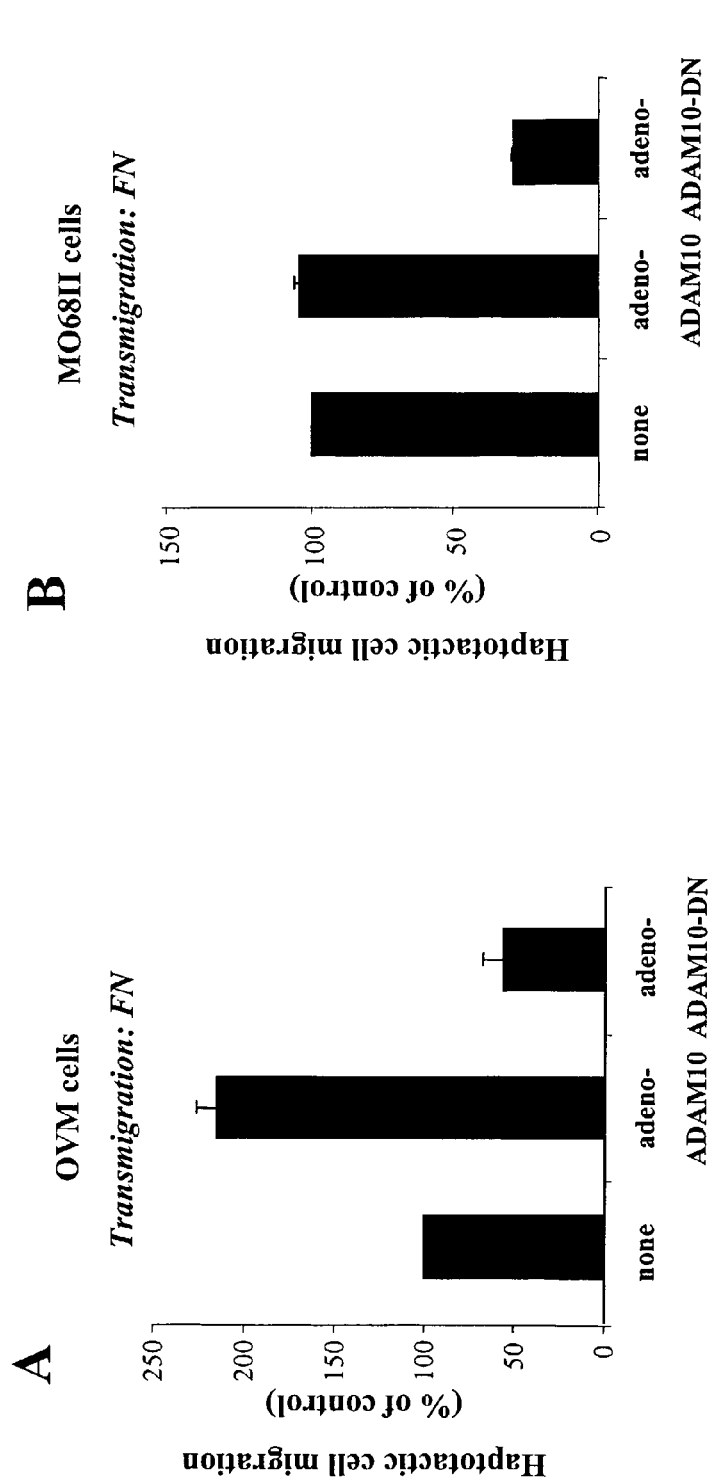

FIG. 13 L1-dependent migration of carcinoma cells is suppressed by adenoviral dominant-negative ADAM-10

(A,B) Infection of L1 positive ovarian carcinoma cells OVM and MO68 with adeno ADAMD10 augments cell migration. In contrast, infection with adeno ADAM10-DN has a suppressive effect. The migration assays were carried out as described in the legend to FIG. 9.

Thus, the present invention relates to a pharmaceutical composition comprising (a) compound(s) interfering with the biological activity of L1 and/or ADAM10 or their expression. Preferably, said pharmaceutical composition comprises a combination of compounds interfering with the biological activity of L1 and ADAM10 or their expression.

The term "interfering" as used herein means modulating, preferably reducing or eliminating, the biological activity of L1 and/or ADAM10 or their expression. The modulation of the biological activity can be effected by direct interaction or binding of a compound to L1 and/or ADAM10 or by indirect interaction, e.g., by interacting with a compound that is associated with the biological activity of L1 and/or ADAM10, respectively. The modulation of biological activity can also be achieved by the application of altered, e.g., inactive forms of L1 and/or ADAM10, preferably in excess.

Examples of suitable compounds interfering with the biological activity of L1 and/or ADAM10 with the aim to get a therapeutic effect are:

(a) Plasmids, vectors or natural/synthetic/mutated viruses, oligonucleotides of various types of modification (e.g. PTO, LNA, 2'F-ANA, protein-nucleotide complexes, $RNA_i$, $_{si}RNA$ or $mikro_{mi}RNA$, Methylmetoxy-, Phosphoroamidates, PNA, Morpholino, Phosphoramidate, Cyclohexen (CeNA), gapmeres, ribozymes, aptamers, CpG-oligos, DNA-zymes, riboswitches, or lipids or lipid containing molecules;

(b) peptides, peptide complexes, including all types of linkers, (c) small molecules;

(d) antibodies and their derivatives, especially chimeras, Fab-fragments, Fc-fragments, or (e) carriers, liposomes, nanoparticles, complexes, or any other delivery systems containing the above named constructs.

Further compounds suitable for the purposes of the present invention and methods how to identify/select such compounds are in more detail described below.

Preferably, in a pharmaceutical composition, such compounds as described above are combined with a pharmaceutically acceptable carrier. "Pharmaceutically acceptable" is meant to encompass any carrier, which does not interfere with the effectiveness of the biological activity of the active ingredient and that is not toxic to the host to which it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and the active compound can be administered to the subject at an effective dose.

An "effective dose" refers to an amount of the active ingredient that is sufficient to affect the course and the severity of the disease, leading to the reduction or remission of such pathology. An "effective dose" useful for treating and/or preventing these diseases or disorders may be determined using methods known to one skilled in the art (see for example, Fingl et al., The Pharmacological Basis of Therapeutics, Goodman and Gilman, eds. Macmillan Publishing Co., New York, pp. 1-46 ((1975)).

Administration of the suitable compositions may be effected by different ways, e.g. by intravenous, intraperetoneal, subcutaneous, intramuscular, topical or intradermal administration. The route of administration, of course, depends on the kind of therapy and the kind of compound contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind of therapy, general health and other drugs being administered concurrently.

The person skilled in the art can easily identify or generate compounds useful for the treatments of the present invention based on the knowledge of the amino acid sequence of L1 and ADAM10, respectively, and the nucleotide sequences of the genes encoding these proteins. Respective sequences are found in the NCBI data base:human L1-CAM_NM-000425 (SEQ ID NO: 1); human ADAM10, NM-001110 (SEQ ID NO: 2).

In a further preferred embodiment of the present invention, the compound useful for reducing or inhibiting the expression of the genes encoding L1 and/or ADAM10 is an antisense oligonucleotide or siRNAs specific for ADAM10 and/or L1.

The generation of suitable antisense oligonucleotides includes determination of a site or sites within the L1/ADAM10 genes for the antisense interaction to occur such that the desired effect, e.g., inhibition of expression of the protein, will result. A preferred intragenic site is (a) the region encompassing the translation initiation or termination codon of the open reading frame (ORF) of the gene or (b) a region of the mRNA which is a "loop" or "bulge", i.e., not part of a secondary structure. Once one or more target sites have been identified, oligonucleotides are chosen which are sufficiently complementary to the target, i.e., hybridize sufficiently well and with sufficient specificity, to give the desired effect. In the context of this invention, "hybridization" means hydrogen bonding, which may be Watson-Crick, Hoogsteen or reversed Hoogsteen hydrogen bonding, between complementary nucleoside or nucleotide bases. "Complementary" as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound does not need to be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., in the case of therapeutic treatment.

The skilled person can generate antisense compounds according to the present invention on the basis of the known DNA sequences for L1 and/or ADAM10, respectively.

"Oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. While antisense oligonucleotides are a preferred form of the antisense compound, the present invention comprehends other oligomeric antisense compounds, including but not limited to oligonucleotide mimetics such as are described below. The antisense compounds in accordance with this invention comprise from about 8 to about 50 nucleobases (i.e. from about 8 to about 50 linked nucleosides). Particularly preferred antisense compounds are antisense oligonucleotides, even more preferably those comprising from about 15 to about 25 nucleobases. Antisense compounds include ribozymes, external guide sequences (EGS), oligonucleotides (oligozymes), and other short catalytic RNAs or catalytic oligonucleotides which hybridize to the target nucleic acid and inhibit its expression.

Alternatively, the pharmaceutical composition of the invention contains a vector allowing to transcribe an antisense oligonucleotide of the invention, e.g., in a mammalian host. Preferably, such a vector is a vector useful for gene therapy. Preferred vectors useful for gene therapy are viral vectors, e.g. adenovirus, herpes virus, vaccinia, or, more preferably, an RNA virus such as a retrovirus. Even more preferably, the retroviral vector is a derivative of a murine or avian retrovirus. Examples of such retroviral vectors which can be used in the present invention are: Moloney murine leukemia virus (Mo-MuLV), Harvey murine sarcoma virus (HaMuSV), murine mammary tumor virus (MuMTV) and Rous sarcoma virus (RSV). Most preferably, a non-human primate retroviral vector is employed, such as the gibbon ape leukemia virus (GaLV), providing a broader host range compared to murine vectors. Since recombinant retroviruses are defective, assistance is required in order to produce infectious particles. Such assistance can be provided, e.g., by using helper cell lines that contain plasmids encoding all of the structural genes of the retrovirus under the control of regulatory sequences within the LTR. Suitable helper cell lines are well known to those skilled in the art. Said vectors can additionally contain a gene encoding a selectable marker so that the transduced cells can be identified. Moreover, the retroviral vectors can be modified in such a way that they become target specific. This can be achieved, e.g., by inserting a polynucleotide encoding a sugar, a glycolipid, or a protein, preferably an antibody. Those skilled in the art know additional methods for generating target specific vectors. Further suitable vectors and methods for in vitro- or in vivo-gene therapy are described in the literature and are known to the persons skilled in the art; see, e.g., WO 94/29469 or WO 97/00957.

In order to achieve expression only in the target organ, e.g., ovarian or endometrial carcinoma, the DNA sequences for transcription of the antisense oligonucleotides can be linked to a tissue specific promoter and used for gene therapy. Such promoters are well known to those skilled in the art (see e.g. Zimmermann et al., (1994) Neuron 12, 11-24; Vidal et al.; (1990) EMBO J. 9, 833-840; Mayford et al., (1995), Cell 81, 891-904; Pinkert et al., (1987) Genes & Dev. 1, 268-76).

Within an oligonucleotide structure, the phosphate groups are commonly referred to as forming the internucleoside backbone of the oligonucleotide. The normal linkage or backbone of RNA and DNA is a 3' to 5' phosphodiester linkage. Specific examples of preferred antisense compounds useful in the present invention include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotide backbones which can result in increased stability are known to the person skilled in the art, preferably such modification is a phosphorothioate linkage.

A preferred oligonucleotide mimetic is an oligonucleotide mimetic that has been shown to have excellent hybridization properties, and is referred to as a peptide nucleic acid (PNA).

In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone (see, e.g., Nielsen et al., Science 254 (1991), 1497-1500.)

Modified oligonucleotides may also contain one or more substituted or modified sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. A particularly preferred modified sugar moiety is a 2'-O-methoxyethyl sugar moiety.

Oligonucleotides of the invention may also include nucleobase modifications or substitutions. Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine etc., with 5-methylcytosine substitutions being preferred since these modifications have been shown to increase nucleic acid duplex stability.

Another modification of the oligonucleotides of the invention involves chemically linking to the oligonucleotide one or more moieties or conjugates which enhance the activity, cellular distribution or cellular uptake of the oligonucleotide. Such moieties include lipid moieties such as a cholesterol moiety, cholic acid, a thioether, a thiocholesterol, an aliphatic chain, e.g., dodecandiol or undecyl residues, a phospholipid, a polyamine or a polyethylene glycol chain, or adamantane acetic acid, a palmityl moiety, or an octadecylamine or hexylamino-carbonyl-oxycholesterol moiety.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers.

In a further preferred embodiment of the present invention, the compounds useful for interfering with the biological activity of L1 and/or ADAM10 are compounds reducing or inhibiting the biological activity of L1 and/or ADAM10.

Preferred examples of such compounds are (neutralizing) antibodies directed against L1 and/or ADAM10. The term "antibody", preferably, relates to antibodies which consist essentially of pooled monoclonal antibodies with different epitopic specifities, as well as distinct monoclonal antibody preparations. Monoclonal antibodies are made from an antigen containing, e.g., a fragment of L1 or ADAM10 by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab')2 fragments) which are capable of specifically binding to protein. Fab and F(ab')2 fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a FAB or other immunoglobulin expression library.

Moreover, antibodies useful for the purposes of the present invention include chimerical, single chain, and humanized antibodies.

Alternatively, preferred compounds for the purpose of the invention are inactive versions of L1 and/or ADAM10 or genes encoding inactive versions of L1 and/or ADAM10. Such inactive versions can be generated according to well known methods of mutagenesis and, e.g., described in Example 7 of the invention. Such compounds can have a therapeutic effect in the human body by displacing their functionally active counterpart, in particular when applied in excess. A preferred example of an inactive version of L1 is a mutated form of L1, wherein the putative SH3 binding site of L1, TSPINP (SEQ ID NO: 7) at positions 1247-1252, has been mutated to AAPINP (SEQ ID NO: 8).

The pharmaceutical composition of the present invention may also comprise a mixture of compounds as defined above, e.g., an antibody directed against L1 and/or an antisense oligonucleotide directed against ADAM10 expression, an inactive version of ADAM10 and an antisense oligonucleotide directed against L1 expression, etc.

The present invention also relates to various therapeutic uses of the compounds of the invention, i.e. for the prevention or treatment of a disease characterized by abnormal proliferation of cells, preferably a carcinoma with ovarian and endometrial carcinomas being particularly preferred.

The present invention also relates to a method for identifying a compound interfering with the biological activity of L1 and/or ADAM10 or their expression, comprising the steps of:
  (a) incubating a candidate compound with a test system comprising L1 and/or/or ADAM10 or their genes; and
  (b) assaying a biological activity of L1 and/or ADAM10; wherein an inhibition or loss of a biological activity of L1 and/or ADAM10 compared to a test system in the absence of said test compound is indicative of the presence of a candidate compound having the desired properties.

Examples of such candidate molecules include antibodies, oligonucleotides, proteins, or small molecules. Such molecules can be rationally designed using known techniques.

Preferably, said test system used for screening comprises substances of similar chemical and/or physical properties, most preferably said substances are almost identical. The compounds which can be prepared and identified according to a use of the present invention may be expression libraries, e.g., cDNA expression libraries, peptides, proteins, nucleic acids, antibodies, small organic compounds, ligands, hormones, peptidomimetics, PNAs or the like.

WO 98/25146 describes further methods for screening libraries of complexes for compounds having a desired property, especially, the capacity to agonize, bind to, or antagonize a polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with L1/ADAM10 or nucleic acid molecules encoding such molecules are, for example, the in vitro screening with the phage display system as well as filter binding assays or "real time" measuring of interaction using, for example, the BIAcore apparatus (Pharmacia).

It is also well known to the person skilled in the art, that it is possible to design, synthesize and evaluate mimetics of small organic compounds that, for example, can act as a substrate or ligand to L1/ADAM10. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987.

All these methods can be used in accordance with the present invention to identify a compound interfering with the biological activity of L1/ADAM10 or their expression.

The genes encoding L1 and/or ADAM10 can also serve as a target for screening inhibitors. Inhibitors may comprise, for example, proteins that bind to the mRNA of the genes encoding L1 and/or ADAM10, thereby destabilizing the native conformation of the mRNA and hampering transcription and/or translation. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical interest, and for identifying unknown RNA targets for use in treating a disease. These methods and compositions can be used for identifying compounds useful to reduce expression levels of L1 and/or ADAM10.

The compounds which can be tested and identified according to the method of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of L1/ADAM10 and/or which exert their effects up- or downstream of L1/ADAM10 may be identified using, for example, insertion mutagenesis using, for example, gene targeting vectors known in the art. Said compounds can also be functional derivatives or analogues of known inhibitors. Such useful compounds can be for example transacting factors which bind to L1/ADAM10 or regulatory sequences of the gene encoding it. Identification of transacting factors can be carried out using standard methods in the art. To determine whether a protein binds to the protein itself or regulatory sequences, standard native gel-shift analyses can be carried out. In order to identify a transacting factor which binds to the protein or regulatory sequence, the protein or regulatory sequence can be used as an affinity reagent in standard protein purification methods, or as a probe for screening an expression library. The identification of nucleic acid molecules which encode polypeptides which interact with L1 and/or ADAM10, respectively, can also be achieved, for example, as described in Scofield (Science 274 (1996), 2063-2065) by use of the so-called yeast "two-hybrid system". In this system L1 or ADAM10 is linked to the DNA-binding domain of the GAL4 transcription factor. A yeast strain expressing this fusion polypeptide and comprising a lacZ reporter gene driven by an appropriate promoter, which is recognized by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of, e.g., L1 or ADAM10, the complex is able to direct expression of the reporter gene. In this way, e.g., L1/ADAM10 and the gene encoding L1/ADAM10 can be used to identify peptides and proteins interacting with L1 or ADAM10. It is apparent to the person skilled in the art that this and similar systems may then further be exploited for the identification of inhibitors.

Finally, the present invention relates to the use of compounds identified by the methods described above interfering with the biological activity of L1 and/or ADAM10 for the preparation of a pharmaceutical composition for the prevention or treatment of a disease characterized by abnormal cell proliferation, e.g., the diseases described above.

Moreover, the present invention also relates to a diagnostic composition comprising compounds which are capable of specifically (a) binding to L1 and/or ADAM10 or (b) hybridizing to the mRNAs encoding L1 and/or ADAM10. Preferably, said compounds are nucleic acid molecules or antibodies as already defined above.

The nucleic acid molecules also comprise primers for PCR. The person skilled in the art is in a position to design suitable nucleic acids probes based on the information as regards the nucleotide sequence of L1 and ADAM10 and the description of oligonucleotides provided above (e.g., as regards complementarity, lengths etc.). For evaluating whether the concentrations of L1 and/or ADAM10 encoding mRNAs (or the translated proteins) are decreased or increased, the measured concentrations are compared with the concentration in a normal tissue. In order to restrict hybridisation of the probe to mRNA(s), i.e. to avoid hybridisation with the corresponding DNA which lead to incorrect results, the sample can, e.g., treated with DNAse I.

The probes (nucleic acid molecules or antibodies) can be detectably labelled, for example, with a radioisotope, a bioluminescent compound, a chemiluminescent compound, a fluorescent compound, a metal chelate, or an enzyme.

The expression of L1 and ADAM10 in tissues can be studied with classical immunohistological methods. Other antibody based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin. In addition to assaying L1/ADAM10 levels in a biological sample, L1/ADAM10 can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labelling of nutrients for the relevant hybridoma. A protein-specific antibody or antibody fragment which has been labelled with an appropriate detectable imaging moiety, such as a radioisotope (for example, $^{131}$I, $^{112}$In, $^{99}$mTc), a radio-opaque substance, or a material detectable by nuclear magnetic resonance, is introduced (for example, parenterally, subcutaneously, or intraperitoneally) into the patient. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labelled antibody or antibody fragment will then preferentially accumulate at the location of cells which contain the specific DSM-protein.

Finally, the present invention relates to the use of the diagnostic compounds defined above for the preparation of a diagnostic composition for the diagnosis of highly malignant forms of a carcinoma, preferably an ovarian or endometrial carcinoma.

The below example explains the invention in more detail.

Example 1

Material and Methods (A) Cells and Antibodies The ovarian tumor cell lines OVMz, SKOV3ip, OAW 42, Chinese hamster ovary cells (CHO) cells stably transfected with human L1 (CHO-hL1) were described (Mechtersheimer et al., supra; Gutwein et al., supra). Other lines (GG, M130) were obtained from Dr. Brigitte Gackel, University of Tubingen. The human epithelial kidney cell line HEK-293 or CHO cells stably expressing human L1 (HEK-hL1) or hL1mutSH3 were established by transfection with superfect (Stratagene, Heidelberg, Germany) and selection of L1 with mAb L1-11A and magnetic beads (Myltenyi Biotec, Bergisch Gladbach, Germany). All cells were cultivated in DMEM supplemented with 10% FCS at 37° C., 5% $CO_2$ and 100% humidity. Antibodies to L1 (mAb L1-11A to the ectodomain and anti pcytL1 against the cytoplasmic portion) and ADAM10 ectodomain (#2547) were described (Gutwein et al., supra). Additional polyclonal antibodies to ADAM17 and ADAM10 were obtained from Chemicon [http://www.chemicon.com/]. Antibodies to βvβ3 and βvβ5 integrins were from Chemicon, the mAb to β5-integrin (SAM-1) and β6-integrin (Groh-1) were from Coulter-Immunotech (Krefeld, Germany). Cells were cultivated in DMEM supplemented with 10% FCS at 37° C., 5% $CO_2$ and 100% humidity.

(B) Tumor Specimens

Peritoneal fluid specimens were obtained from a patient who had histologically confirmed epithelial ovarian carcinoma. Ovarian carcinoma cells from the ascites were isolated by density centrifugation using Ficoll separation solution (Biochrom, Berlin, Germany) at 400 g for 30 min. Briefly, the cells in the interface were collected, washed in phosphate-buffered saline, counted by trypan blue exclusion and sorted by flow cytometry for Ep-CAM expressing cells using mAb Hea-125 (kind gift from Dr. Gerd Moldenhauer, German Cancer Research Center). Isolated cells were grown in RPMI medium supplemented with 20% FCS and processed for further experiments. The cell line MO68 II was used between passage numbers 3-8.

Peritoneal mesothelial cells were cultured from the ascites of cancer patients. Cells in ascites fluid were collected by centrifugation and seeded in WF-Medium (DMEM with 10% FCS, 1% penicillin/streptomycin, 1% Hepes and 1% WF-supplement). Cells were allowed to adhere to tissue culture plastic for 2 h. Non-adherent cells were removed by rinsing with PBS. Adherent cells were cultured in WF-Medium and expanded for about 2-3 passages before use. Patient material was obtained under the approval of the ethic commitee of the University of Heidelberg.

(C) DNA

Human L1 encoding plasmids were obtained from Dr. Vance Lemmon (University of Miami, Miami, Fla., USA). A cDNA encoding FLAG-tagged L1 was constructed by PCR. Plasmids encoding HA-tagged ADAM10 and a FLAG-tagged dominant-negative form of ADAM10 (ADAM10 DN) (Lammich et al., Proc. Natl. Acad. Sci. USA 96 (1999), 3922-7) were provided by Dr. Falk Fahrenholz (University of Mainz, Germany). Mutagenesis of amino acids in the cytoplasmic portion of L1 to produce hL1mutSH3 was done using standard molecular biology techniques.

(D) Adenovirus Production

Recombinant adenovirus encoding human L1 was produced as described by the manufacturer (Qbiogene, Heidelberg, Germany). For adenovirus construction, cDNA was cloned into the plasmid pShuttle and recombination was carried out in BJ bacteria. The recombined plasmid was linearized and transfected into QBI 293 cells for virus production. Transfected cells were plated in semisolid agar and colonies were picked after 10 days. Plaque purified virus was amplified in QBI 293 cells and finally purified using the Adeno-X™ virus purification kit as recommended by the manufacturer (BD Bioscience, Heidelberg, Germany). YFP-GPI control adenoviruses were a kind gift from Dr. Patrick Keller (Max-Planck Institute for Cell Biology, Dresden).

(E) Immunofluorescent Staining and FACS Analysis

The staining of cells with mAbs and PE-conjugated goat antibodies to mouse immunoglobulins (SERVA, Heidelberg, Germany) has been described (Mechtersheimer et al., J. Cell Biol. 155 (2001), 661-74). Polyclonal antibody #2547 was detected by Cy3-conjugated goat and rabbit IgG (Molecular Probes). Stained cells were analysed with a FACScan using Cellquest software (Becton & Dickinson, Heidelberg, Germany).

(F) Transmigration Assays

The haptotactic cell migration assay on fibronectin, laminin or BSA was performed in Transwell chambers (Costar, 6.5 mm diameter, 5 um pore size) and was described in detail elsewhere (Mechtersheimer et al., supra). Transmigrated cells were quantified by staining of the transwell membranes with cristalviolet solution as described (Mechtersheimer at al., supra). The eluted dye was measured at 595 nm in an ELISA reader.

(G) Analysis of L1 Shedding

These assays were described previously (Mechtersheimer et al., supra; Lammich et al., supra). Briefly, $2 \times 10^6$ cells were plated in tissue culture plates in complete medium. After 24 hr at 37° C., the medium was replaced by serum-free culture medium for the indicated period of time. Aliquots of the medium were analysed by SDS-PAGE following TCA precipitation (Lammich et al., supra). Treated cells were removed from the tissue culture plastic surface by treatment with PBS/5 mM EDTA. Cell pellets were lysed in lysis buffer (20 mM Tris/HCl, pH 8.0, containing 1% Triton X-100, 150 mM NaCl, 1 mM PMSF), cleared by centrifugation and mixed with twofold-concentrated reducing SDS-sample buffer.

(H) Biochemical Analysis

The isolation of soluble L1 was described by Mechtersheimer, supra. Briefly, ascites was centrifuged at 3000×g for 15 min and loaded on a 35% sucrose/H₂O cushion. After centrifugation for 3 h at 35000×g the cleared ascites fluid was adsorbed to Sepharose-linked mAb L1-11A and soluble L1 was purified as previously described (Ruppert et al., J. Cell. Biol. 131 (1995), 1881-91). Aliquots of the samples were separated by SDS-PAGE under reducing conditions and transfered to an Immobilon membrane using semi-dry blotting. After blocking with 5% skim milk in TBS, the blots were developed with the respective primary antibody followed by peroxidase conjugated secondary antibody and ECL detection.

(I) Immunohistochemistry

Immunohistochemical staining was performed on 4 um thick sections of formalin fixed, paraffin embedded tissues as previously described (Fogel et al., Lancet 362 (2003), 869-75).

(K) Statistical Analysis

For the analysis of statistical significance the Wilcoxon rank sum/Mann Whitney U test (two-sided) was used.

Examples 2 to 6

The aim of these studies was to investigate the functional relevance of L1, ADAM10 and L1 shedding in ovarian tumor cell lines. The results suggest that L1 expression and shedding could promote metastasis of ovarian tumors by facilitating the adhesion and by enhancing the migratory properties on extracellular matrix components.

Example 2

L1 is Expressed in Ovarian Tumor Lines

Figure 1:
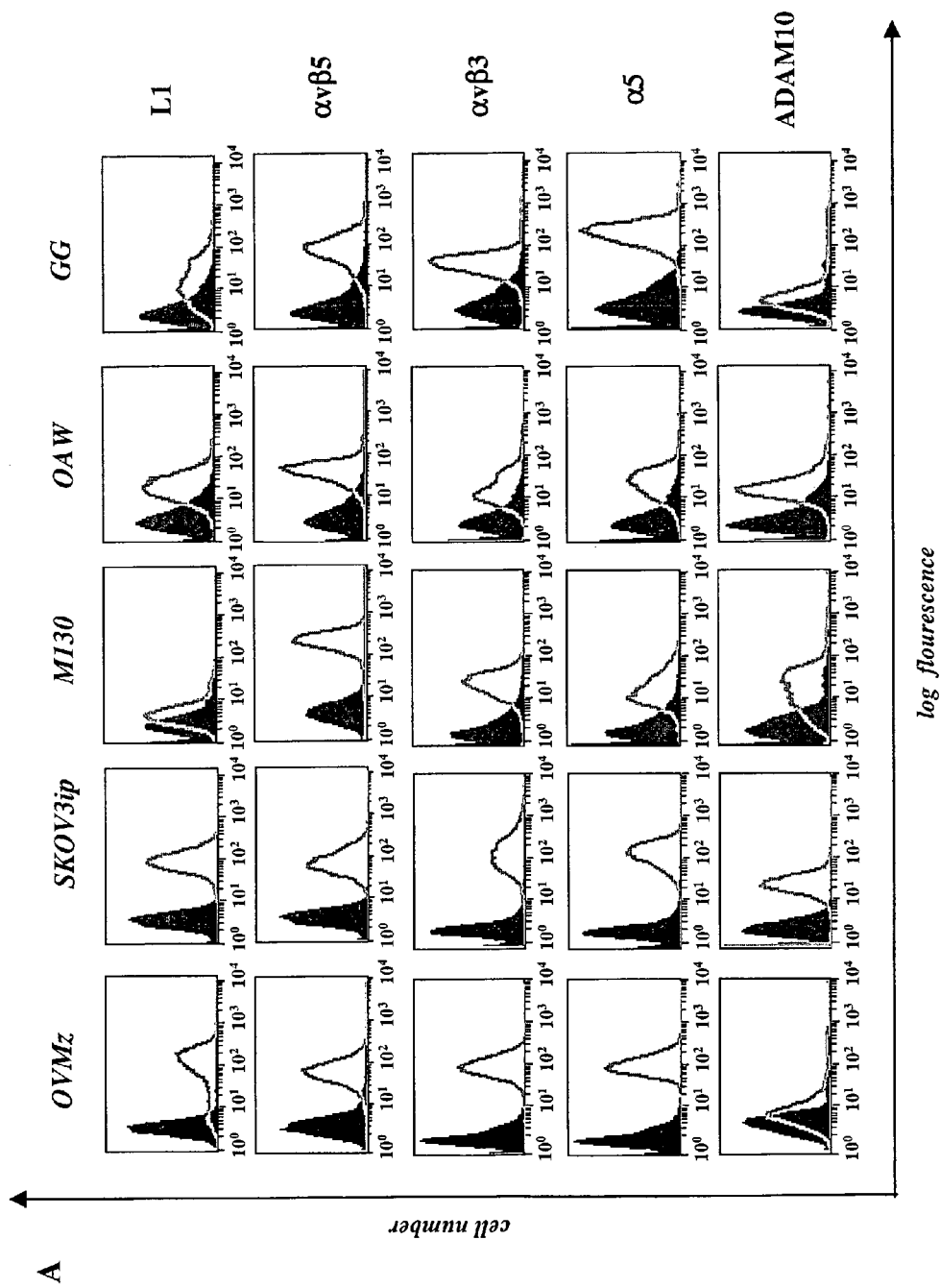
FIG. 1: L1 and ADAM10 in human ovarian tumor cell lines and tumor tissues (A) The indicated ovarian carcinoma cell lines were analysed by cytofluorographic analysis using mAb L1-11AL1-11A to L1 and mAbs to the indicated integrins followed by PE-conjugated secondary antibody to mouse IgG. For ADAM10 detection the antibody #2547 followed by Alexa488-conjugated goat anti-rabbit IgG was used.
Figure 1:
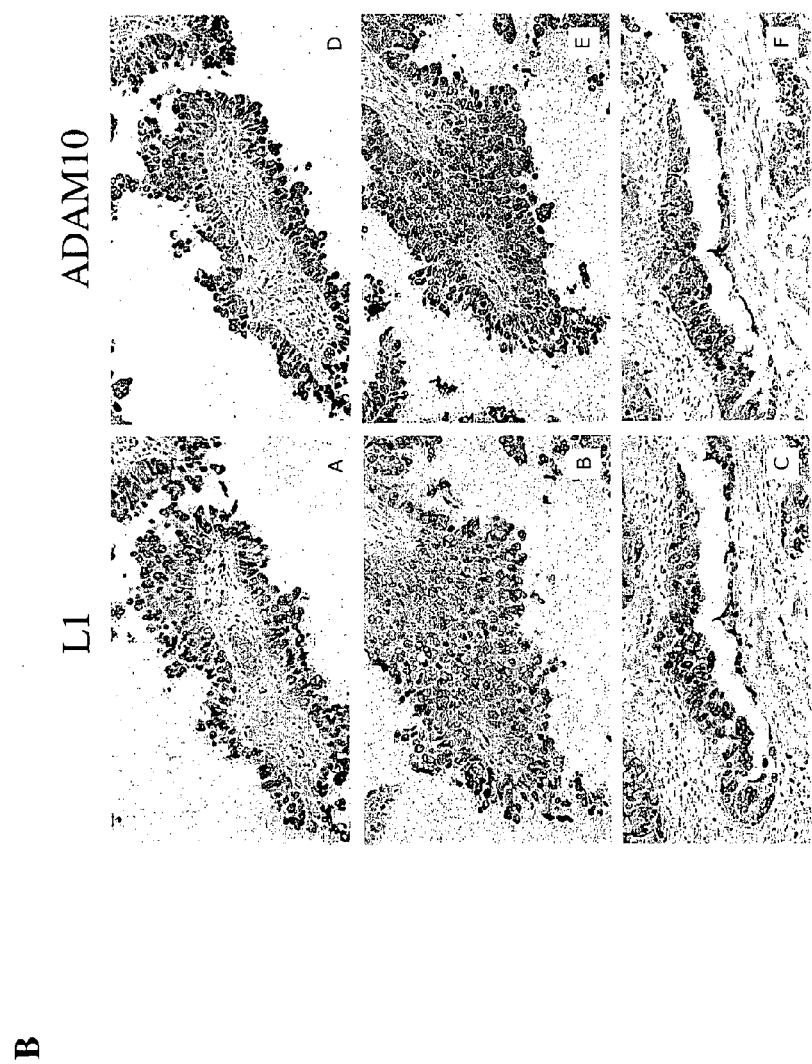

To elucidate the functional role of L1, ovarian carcinoma cell lines were screened for L1 expression. Out of 5 tested lines, the cell lines OVMz, SKOV3ip, and OAW 42 were strongly positive for L1 whereas GG and M130 cells were almost negative (FIG. 1A). The tumor cell lines were positive for $\beta v\beta 3$ and $\beta v\beta 5$ integrins and expressed the 35 integrin subunit at variable levels (FIG. 1A). All cells expressed the metalloproteinase ADAM10 at the cell surface (FIG. 1A). Co-expression of L1 and ADAM10 was confirmed in paraffin-embedded sections of patient derived ovarian carcinomas (FIG. 1B).

Example 3

L1 Overexpression and Cell Migration

L1 has an important role in promoting cell migration. As it was already demonstrated, L1 overexpression enhances the haptotactic cell migration of CHO cells. To extend these observation, HEK293 cells were stably transfected with FLAG-L1 (HEK293-hL1). L1 expression was confirmed by FACS analysis using an L1 specific antibody (FIG. 2A). Alternatively, Western blot analysis of the cell lysate ensured the presence of full-length L1-220 and of the cleavage products L1-85, L1-42 and L1-32 (FIG. 2B). When transfected and non-transfected cells were tested for haptotactic migration using fibronectin as substrate, the L1-expressing cells exhibited a 5-fold enhanced migration factor compared to controls (FIG. 2C). Similar results were obtained when laminin was used as substrate (data not shown). The enhanced migration was blocked in the presence of mAbs against the integrins $\alpha 5\beta 1$ and $\alpha v\beta 5$ but only weakly affected by a mab to $\alpha v\beta 3$ (FIG. 2C). The basal migration of HEK293 cells was only inhibited by the mAb to $\alpha 5\beta 1$ integrin (FIG. 2C). In agreement with previous findings, it was observed that the addition of soluble L1-Fc but not control-Fc to HEK293 cells augmented the migration of the cells to a similar extend as L1 transfection (FIG. 2D).

To allow rapid overexpression in ovarian carcinoma cells, a recombinant adenovirus encoding L1 was constructed. As shown in FIG. 3A, the infection of M130 and GG with adeno-L1 increased L1 cell surface expression as detected by fluorescent staining. Likewise, the amount of L1 and its cleavage products in the cell lysate was enhanced in a dose dependent manner (FIG. 3B) and the release of soluble L1-200 into the medium was augmented (FIG. 3C).

The effect of adeno-L1 on migration using fibronectin as substrate was examined. As shown in FIG. 3D, infection of the ovarian cell lines GG with adeno-L1 significantly enhanced migration. This effect was not seen with the control YFP-TM adenovirus ruling out the possibility that enhanced migration was due to viral infection (FIG. 3D). Soluble L1 released to the supernatant of infected GG cells was able to stimulate the migration of HEK293 cells (FIG. 3E). Enhanced migration following adeno-L1 infection was also seen when OVMz, SKOV3ip or M130 were analysed for migration on fibronectin (data not shown). Collectively, these results suggest that L1 in a cell surface or soluble form can stimulate the migration of ovarian carcinoma cells.

Example 4

Soluble L1 in the Ascites of Ovarian Cancer Patients

Soluble L1 was observed in the sera but also in the ascites of advanced ovarian carcinoma patients. Affinity purified L1 from ascites fluid was found to be intact and undegraded with a size of 150 kDa (L1-150) and 200 kDa (L1-200) (FIG. 4A). To analyse the ascites derived L1 in functional terms, HEK293 cells were stimulated to migrate using fibronectin as substrate. As shown in FIG. 4B, the soluble L1 was a potent dose-dependent inducer of cell migration. Again, the enhanced cell migration was blocked in the presence of a mAb to the $\alpha 5\beta 1$ and $\alpha v\beta 5$ integrin, but only little effect was seen with the mAb to $\alpha v\beta 3$ (FIG. 4C).

Example 5

Expression of a Dominant-negative Form of ADAM10 Reduces Cell Migration

Here it is demonstrated that HEK293-hL1 cells transiently expressing ADAM10-DN (having the mutation E 384A within the catalytic domain) had a significantly decreased migration on fibronectin (p=0.029) whereas overexpression of ADAM10 augmenting this effect (p=0.029) (FIG. 5A). Expression of ADAM10 or ADAM10-DN had no effect on the basal cell migration of HEK293 cells. Similar results were obtained when laminin was used as a substrate (not shown). To rule out the possibility that the transfection had disturbed integrin function, the cell adhesion to fibronectin was also tested. As shown in FIG. 5B, the adhesion was very similar between transfected and non-tranfected cells. These results suggested that the ADAM10 proteolytic activity was an important component of L1-enhanced migration.

Example 6

Functionally Inactive Forms of L1 and ADAM10 can be Used to Silence Important Proteins Vital for Ovarian Carcinoma Cell Function L1 carries several putative phosphorylation sites in the cytoplasmic tail of which have been attributed to known kinases and published evidence is shown in FIG. 7. The putative SH3 binding site TSPINP was mutated into AAPINP (positions 1247 and 1248) using standard laboratory methods of mutagenesis. The putative SH3 binding site has been proposed to be phosphorylated by erk-kinase. The resulting mutant was termed hL1-mutSH3 (humanL1 mutated in SH3 binding site). Both wildtype L1 (non-mutated) and L1mutSH3 cDNAs were stably transfected in CHO (chinese hamster ovary) and HEK (human embryonic kidney) 293 cells. The transfectants were analysed by immunofluorescent staining and cytofluorographic analysis using an antibody to human L1.

As shown in FIGS. 8 A and B, L1 wildtype and hL1mutSH3 revealed L1 expression at similar levels. Additional biochemical analysis showed that both forms of L1 were processed and cleaved to similar extend (FIGS. 8 C and D).

Expression of L1 renders the cells more motile on various extracellular matrix proteins (ECM) such as fibronectin, laminin and vitronectin (Mechtersheimer et al., supra). Thus, L1 wildtype and hL1mutSH3 cells were compared for the ability to migrate on fibronectin and laminin. As shown in FIG. 9, both CHO-hL1mutSH3 and HEK293-hL1mutSH3 cells did not migrate whereas the L1 wild type transfected cells were able to migrate as expected.

Then, it was analysed whether HEK-293-hL1mutSH3 cells could be induced to migrate on fibronectin. As shown in FIG. 10A, the addition of soluble recombinant L1 induced migration of HEK293 cells as expected but was unable to induce migration of HEK293-hL1mutSH3 cells. It was also tested whether soluble L1 released from HEK293-hL1mutSH3 cells was functionally active in inducing cell migration. As shown in FIG. 10B, the supernatant collected from the cells was able to induce migration of normal HEK293 cells. It can be concluded that HEK-293-hL1mutSH3 cells are refractory to the induction of migration by soluble L1. The released L1 is functionally intact.

Next the ability of hL1mutSH3 to suppress the enhanced migration of L1 wild type cells was tested. Such an ability is termed a dominant-negative effect and is based on the competition between wild type (functionally active) and mutant molecules (functionally inactive). As shown in FIG. 11, the transient expression of hL1mutSH3 but not control vector (pcDNA3) could block the enhanced migration of HEK-293-hL1 (wild type) cells. The same effect was observed with a dominant-negative form of the L1 shedding protease ADAM10 (ADAM10-DN) and the erk-kinase specific inhibitor PD59098.

To allow rapid expression of hL1mutSH3 and ADAM10-DN in ovarian carcinomas, both cDNAs were expressed as recombinant adenovirus. To investigate the effect of hL1mutSH3 adeno infected 3 L1 positive ovarian carcinomas were transfected with the recombinant virus and analysed the migration on fibronectin 48 hr later. As shown in FIGS. 12B-D, the 3 ovarian carcinomas OVM, SKOV3 and Mo68 showed a significant reduction in cell migration (between 50-70% inhibition) whereas wild type L1 adeno lead to enhanced migration (appr. 30% enhancement). There was no inhibition of cell migration by hL1mutSH3-adeno in the L1-negative cell line KS (FIG. 12A). However, the wildtype L1 adeno showed a very strong augmenting effect (appr. 130%). This observation suggested that hL1mutSH3 was only active in L1 positive cells and was competing for endogenous L1 in the carcinoma cells.

As shown in FIG. 13, also ADAM10-DN-adeno was able to block the enhanced migration of the two ovarian carcinoma cell lines investigated. These experiments indicated that functionally inactive forms of L1 and ADAM10 can be used to silence important proteins vital for ovarian carcinoma cell function.

The invention claimed is:

1. A pharmaceutical composition comprising an inactive version of human L1-CAM and a pharmaceutically acceptable carrier, wherein said inactive version of human L1-CAM has the sequence of SEQ ID NO: 1, except in which TSPINP (SEQ ID NO: 7) at amino acid positions 1247-1252 have been mutated to AAPINP (SEQ ID NO: 8).

2. The pharmaceutical composition of claim 1 further comprising an inactive version of ADAM10 that interferes with the biological activity of ADAM10, wherein said inactive version of ADAM10 has the sequence of SEQ ID NO: 2, except it carries a mutation E384A within its catalytic domain.

3. The pharmaceutical composition of claim 1, further comprising antisense oligonucleotides reducing or inhibiting the expression of the gene(s) encoding ADAM10.

4. The pharmaceutical composition of claim 1, further comprising antibodies directed against ADAM10.

5. A method for treating carcinoma comprising administering the pharmaceutical composition of claim 1 to a subject in need thereof.

6. The method according to claim 5, wherein said carcinoma is an ovarian or endometrial carcinoma.

7. The pharmaceutical composition of claim 1, further comprising a compound interfering with the biological activity of L1 and/or ADAM10 selected from the group consisting of (a) an antisense oligonucleotide specific for L1 and/or ADAM10, and (b) an antibody directed against L1 and/or ADAM10.

* * * * *

SEQUENCE LISTING

<160> NUMBER OF SEQ ID NOS: 8

<210> SEQ ID NO 1
<211> LENGTH: 1257
<212> TYPE: PRT
<213> ORGANISM: homo sapiens

<400> SEQUENCE: 1

```
Met Val Val Ala Leu Arg Tyr Val Trp Pro Leu Leu Leu Cys Ser Pro
1               5                   10                  15

Cys Leu Leu Ile Gln Ile Pro Glu Glu Tyr Glu Gly His His Val Met
                20                  25                  30

Glu Pro Pro Val Ile Thr Glu Gln Ser Pro Arg Arg Leu Val Val Phe
            35                  40                  45

Pro Thr Asp Asp Ile Ser Leu Lys Cys Glu Ala Ser Gly Lys Pro Glu
        50                  55                  60

Val Gln Phe Arg Trp Thr Arg Asp Gly Val His Phe Lys Pro Lys Glu
65                  70                  75                  80

Glu Leu Gly Val Thr Val Tyr Gln Ser Pro His Ser Gly Ser Phe Thr
                85                  90                  95

Ile Thr Gly Asn Asn Ser Asn Phe Ala Gln Arg Phe Gln Gly Ile Tyr
            100                 105                 110

Arg Cys Phe Ala Ser Asn Lys Leu Gly Thr Ala Met Ser His Glu Ile
        115                 120                 125
```

```
Arg Leu Met Ala Glu Gly Ala Pro Lys Trp Pro Lys Glu Thr Val Lys
    130                 135                 140
Pro Val Glu Val Glu Glu Gly Glu Ser Val Val Leu Pro Cys Asn Pro
145                 150                 155                 160
Pro Pro Ser Ala Glu Pro Leu Arg Ile Tyr Trp Met Asn Ser Lys Ile
                165                 170                 175
Leu His Ile Lys Gln Asp Glu Arg Val Thr Met Gly Gln Asn Gly Asn
            180                 185                 190
Leu Tyr Phe Ala Asn Val Leu Thr Ser Asp Asn His Ser Asp Tyr Ile
        195                 200                 205
Cys His Ala His Phe Pro Gly Thr Arg Thr Ile Ile Gln Lys Glu Pro
    210                 215                 220
Ile Asp Leu Arg Val Lys Ala Thr Asn Ser Met Ile Asp Arg Lys Pro
225                 230                 235                 240
Arg Leu Leu Phe Pro Thr Asn Ser Ser Ser His Leu Val Ala Leu Gln
                245                 250                 255
Gly Gln Pro Leu Val Leu Glu Cys Ile Ala Glu Gly Phe Pro Thr Pro
            260                 265                 270
Thr Ile Lys Trp Leu Arg Pro Ser Gly Pro Met Pro Ala Asp Arg Val
        275                 280                 285
Thr Tyr Gln Asn His Asn Lys Thr Leu Gln Leu Leu Lys Val Gly Glu
    290                 295                 300
Glu Asp Asp Gly Glu Tyr Arg Cys Leu Ala Glu Asn Ser Leu Gly Ser
305                 310                 315                 320
Ala Arg His Ala Tyr Tyr Val Thr Val Glu Ala Pro Tyr Trp Leu
                325                 330                 335
His Lys Pro Gln Ser His Leu Tyr Gly Pro Gly Glu Thr Ala Arg Leu
            340                 345                 350
Asp Cys Gln Val Gln Gly Arg Pro Gln Pro Glu Val Thr Trp Arg Ile
        355                 360                 365
Asn Gly Ile Pro Val Glu Glu Leu Ala Lys Asp Gln Lys Tyr Arg Ile
    370                 375                 380
Gln Arg Gly Ala Leu Ile Leu Ser Asn Val Gln Pro Ser Asp Thr Met
385                 390                 395                 400
Val Thr Gln Cys Glu Ala Arg Asn Arg His Gly Leu Leu Leu Ala Asn
                405                 410                 415
Ala Tyr Ile Tyr Val Val Gln Leu Pro Ala Lys Ile Leu Thr Ala Asp
            420                 425                 430
Asn Gln Thr Tyr Met Ala Val Gln Gly Ser Thr Ala Tyr Leu Leu Cys
        435                 440                 445
Lys Ala Phe Gly Ala Pro Val Pro Ser Val Gln Trp Leu Asp Glu Asp
    450                 455                 460
Gly Thr Thr Val Leu Gln Asp Glu Arg Phe Phe Pro Tyr Ala Asn Gly
465                 470                 475                 480
Thr Leu Gly Ile Arg Asp Leu Gln Ala Asn Asp Thr Gly Arg Tyr Phe
                485                 490                 495
Cys Leu Ala Ala Asn Asp Gln Asn Asn Val Thr Ile Met Ala Asn Leu
            500                 505                 510
Lys Val Lys Asp Ala Thr Gln Ile Thr Gln Gly Pro Arg Ser Thr Ile
        515                 520                 525
Glu Lys Lys Gly Ser Arg Val Thr Phe Thr Cys Gln Ala Ser Phe Asp
    530                 535                 540
Pro Ser Leu Gln Pro Ser Ile Thr Trp Arg Gly Asp Gly Arg Asp Leu
```

```
              545                 550                 555                 560
Gln Glu Leu Gly Asp Ser Asp Lys Tyr Phe Ile Glu Asp Gly Arg Leu
                565                 570                 575
Val Ile His Ser Leu Asp Tyr Ser Asp Gln Gly Asn Tyr Ser Cys Val
                580                 585                 590
Ala Ser Thr Glu Leu Asp Val Val Glu Ser Arg Ala Gln Leu Leu Val
                595                 600                 605
Val Gly Ser Pro Gly Pro Val Pro Arg Leu Val Leu Ser Asp Leu His
            610                 615                 620
Leu Leu Thr Gln Ser Gln Val Arg Val Ser Trp Ser Pro Ala Glu Asp
625                 630                 635                 640
His Asn Ala Pro Ile Glu Lys Tyr Asp Ile Glu Phe Glu Asp Lys Glu
                645                 650                 655
Met Ala Pro Glu Lys Trp Tyr Ser Leu Gly Lys Val Pro Gly Asn Gln
                660                 665                 670
Thr Ser Thr Thr Leu Lys Leu Ser Pro Tyr Val His Tyr Thr Phe Arg
                675                 680                 685
Val Thr Ala Ile Asn Lys Tyr Gly Pro Gly Glu Pro Ser Pro Val Ser
            690                 695                 700
Glu Thr Val Val Thr Pro Glu Ala Ala Pro Glu Lys Asn Pro Val Asp
705                 710                 715                 720
Val Lys Gly Glu Gly Asn Glu Thr Thr Asn Met Val Ile Thr Trp Lys
                725                 730                 735
Pro Leu Arg Trp Met Asp Trp Asn Ala Pro Gln Val Gln Tyr Arg Val
                740                 745                 750
Gln Trp Arg Pro Gln Gly Thr Arg Gly Pro Trp Gln Glu Gln Ile Val
                755                 760                 765
Ser Asp Pro Phe Leu Val Val Ser Asn Thr Ser Thr Phe Val Pro Tyr
            770                 775                 780
Glu Ile Lys Val Gln Ala Val Asn Ser Gln Gly Lys Gly Pro Glu Pro
785                 790                 795                 800
Gln Val Thr Ile Gly Tyr Ser Gly Glu Asp Tyr Pro Gln Ala Ile Pro
                805                 810                 815
Glu Leu Glu Gly Ile Glu Ile Leu Asn Ser Ser Ala Val Leu Val Lys
                820                 825                 830
Trp Arg Pro Val Asp Leu Ala Gln Val Lys Gly His Leu Arg Gly Tyr
                835                 840                 845
Asn Val Thr Tyr Trp Arg Glu Gly Ser Gln Arg Lys His Ser Lys Arg
850                 855                 860
His Ile His Lys Asp His Val Val Val Pro Ala Asn Thr Thr Ser Val
865                 870                 875                 880
Ile Leu Ser Gly Leu Arg Pro Tyr Ser Ser Tyr His Leu Glu Val Gln
                885                 890                 895
Ala Phe Asn Gly Arg Gly Ser Gly Pro Ala Ser Glu Phe Thr Phe Ser
                900                 905                 910
Thr Pro Glu Gly Val Pro Gly His Pro Glu Ala Leu His Leu Glu Cys
                915                 920                 925
Gln Ser Asn Thr Ser Leu Leu Leu Arg Trp Gln Pro Pro Leu Ser His
            930                 935                 940
Asn Gly Val Leu Thr Gly Tyr Val Leu Ser Tyr His Pro Leu Asp Glu
945                 950                 955                 960
Gly Gly Lys Gly Gln Leu Ser Phe Asn Leu Arg Asp Pro Glu Leu Arg
                965                 970                 975
```

-continued

Thr His Asn Leu Thr Asp Leu Ser Pro His Leu Arg Tyr Arg Phe Gln
            980                 985                 990

Leu Gln Ala Thr Thr Lys Glu Gly Pro Gly Glu Ala Ile Val Arg Glu
        995                 1000                1005

Gly Gly Thr Met Ala Leu Ser Gly Ile Ser Asp Phe Gly Asn Ile
    1010                1015                1020

Ser Ala Thr Ala Gly Glu Asn Tyr Ser Val Val Ser Trp Val Pro
    1025                1030                1035

Lys Glu Gly Gln Cys Asn Phe Arg Phe His Ile Leu Phe Lys Ala
    1040                1045                1050

Leu Gly Glu Glu Lys Gly Gly Ala Ser Leu Ser Pro Gln Tyr Val
    1055                1060                1065

Ser Tyr Asn Gln Ser Ser Tyr Thr Gln Trp Asp Leu Gln Pro Asp
    1070                1075                1080

Thr Asp Tyr Glu Ile His Leu Phe Lys Glu Arg Met Phe Arg His
    1085                1090                1095

Gln Met Ala Val Lys Thr Asn Gly Thr Gly Arg Val Arg Leu Pro
    1100                1105                1110

Pro Ala Gly Phe Ala Thr Glu Gly Trp Phe Ile Gly Phe Val Ser
    1115                1120                1125

Ala Ile Ile Leu Leu Leu Leu Val Leu Leu Ile Leu Cys Phe Ile
    1130                1135                1140

Lys Arg Ser Lys Gly Gly Lys Tyr Ser Val Lys Asp Lys Glu Asp
    1145                1150                1155

Thr Gln Val Asp Ser Glu Ala Arg Pro Met Lys Asp Glu Thr Phe
    1160                1165                1170

Gly Glu Tyr Arg Ser Leu Glu Ser Asp Asn Glu Glu Lys Ala Phe
    1175                1180                1185

Gly Ser Ser Gln Pro Ser Leu Asn Gly Asp Ile Lys Pro Leu Gly
    1190                1195                1200

Ser Asp Asp Ser Leu Ala Asp Tyr Gly Gly Ser Val Asp Val Gln
    1205                1210                1215

Phe Asn Glu Asp Gly Ser Phe Ile Gly Gln Tyr Ser Gly Lys Lys
    1220                1225                1230

Glu Lys Glu Ala Ala Gly Gly Asn Asp Ser Ser Gly Ala Thr Ser
    1235                1240                1245

Pro Ile Asn Pro Ala Val Ala Leu Glu
    1250                1255

<210> SEQ ID NO 2
<211> LENGTH: 748
<212> TYPE: PRT
<213> ORGANISM: homo sapiens

<400> SEQUENCE: 2

Met Val Leu Leu Arg Val Leu Ile Leu Leu Ser Trp Ala Ala Gly
1               5                   10                  15

Met Gly Gly Gln Tyr Gly Asn Pro Leu Asn Lys Tyr Ile Arg His Tyr
            20                  25                  30

Glu Gly Leu Ser Tyr Asn Val Asp Ser Leu His Gln Lys His Gln Arg
        35                  40                  45

Ala Lys Arg Ala Val Ser His Glu Asp Gln Phe Leu Arg Leu Asp Phe
    50                  55                  60

His Ala His Gly Arg His Phe Asn Leu Arg Met Lys Arg Asp Thr Ser
65                  70                  75                  80

```
Leu Phe Ser Asp Glu Phe Lys Val Glu Thr Ser Asn Lys Val Leu Asp
            85                  90                  95
Tyr Asp Thr Ser His Ile Tyr Thr Gly His Ile Tyr Gly Glu Gly
            100                 105                 110
Ser Phe Ser His Gly Ser Val Ile Asp Gly Arg Phe Glu Gly Phe Ile
            115                 120                 125
Gln Thr Arg Gly Gly Thr Phe Tyr Val Glu Pro Ala Glu Arg Tyr Ile
            130                 135                 140
Lys Asp Arg Thr Leu Pro Phe His Ser Val Ile Tyr His Glu Asp Asp
145                 150                 155                 160
Ile Asn Tyr Pro His Lys Tyr Gly Pro Gln Gly Gly Cys Ala Asp His
                    165                 170                 175
Ser Val Phe Glu Arg Met Arg Lys Tyr Gln Met Thr Gly Val Glu Glu
                    180                 185                 190
Val Thr Gln Ile Pro Gln Glu Glu His Ala Ala Asn Gly Pro Glu Leu
            195                 200                 205
Leu Arg Lys Lys Arg Thr Thr Ser Ala Glu Lys Asn Thr Cys Gln Leu
    210                 215                 220
Tyr Ile Gln Thr Asp His Leu Phe Phe Lys Tyr Tyr Gly Thr Arg Glu
225                 230                 235                 240
Ala Val Ile Ala Gln Ile Ser Ser His Val Lys Ala Ile Asp Thr Ile
                245                 250                 255
Tyr Gln Thr Thr Asp Phe Ser Gly Ile Arg Asn Ile Ser Phe Met Val
            260                 265                 270
Lys Arg Ile Arg Ile Asn Thr Thr Ala Asp Glu Lys Asp Pro Thr Asn
            275                 280                 285
Pro Phe Arg Phe Pro Asn Ile Gly Val Glu Lys Phe Leu Glu Leu Asn
    290                 295                 300
Ser Glu Gln Asn His Asp Asp Tyr Cys Leu Ala Tyr Val Phe Thr Asp
305                 310                 315                 320
Arg Asp Phe Asp Asp Gly Val Leu Gly Leu Ala Trp Val Gly Ala Pro
                325                 330                 335
Ser Gly Ser Ser Gly Gly Ile Cys Glu Lys Ser Lys Leu Tyr Ser Asp
            340                 345                 350
Gly Lys Lys Lys Ser Leu Asn Thr Gly Ile Ile Thr Val Gln Asn Tyr
            355                 360                 365
Gly Ser His Val Pro Pro Lys Val Ser His Ile Thr Phe Ala His Glu
    370                 375                 380
Val Gly His Asn Phe Gly Ser Pro His Asp Ser Gly Thr Glu Cys Thr
385                 390                 395                 400
Pro Gly Glu Ser Lys Asn Leu Gly Gln Lys Glu Asn Gly Asn Tyr Ile
                405                 410                 415
Met Tyr Ala Arg Ala Thr Ser Gly Asp Lys Leu Asn Asn Asn Lys Phe
            420                 425                 430
Ser Leu Cys Ser Ile Arg Asn Ile Ser Gln Val Leu Glu Lys Lys Arg
    435                 440                 445
Asn Asn Cys Phe Val Glu Ser Gly Gln Pro Ile Cys Gly Asn Gly Met
450                 455                 460
Val Glu Gln Gly Glu Glu Cys Asp Cys Gly Tyr Ser Asp Gln Cys Lys
465                 470                 475                 480
Asp Glu Cys Cys Phe Asp Ala Asn Gln Pro Glu Gly Arg Lys Cys Lys
                485                 490                 495
Leu Lys Pro Gly Lys Gln Cys Ser Pro Ser Gln Gly Pro Cys Cys Thr
            500                 505                 510
```

-continued

```
Ala Gln Cys Ala Phe Lys Ser Lys Ser Glu Lys Cys Arg Asp Asp Ser
        515                 520                 525
Asp Cys Ala Arg Glu Gly Ile Cys Asn Gly Phe Thr Ala Leu Cys Pro
        530                 535                 540
Ala Ser Asp Pro Lys Pro Asn Phe Thr Asp Cys Asn Arg His Thr Gln
545                 550                 555                 560
Val Cys Ile Asn Gly Gln Cys Ala Gly Ser Ile Cys Glu Lys Tyr Gly
                565                 570                 575
Leu Glu Glu Cys Thr Cys Ala Ser Ser Asp Gly Lys Asp Asp Lys Glu
            580                 585                 590
Leu Cys His Val Cys Cys Met Lys Lys Met Asp Pro Ser Thr Cys Ala
        595                 600                 605
Ser Thr Gly Ser Val Gln Trp Ser Arg His Phe Ser Gly Arg Thr Ile
        610                 615                 620
Thr Leu Gln Pro Gly Ser Pro Cys Asn Asp Phe Arg Gly Tyr Cys Asp
625                 630                 635                 640
Val Phe Met Arg Cys Arg Leu Val Asp Ala Asp Gly Pro Leu Ala Arg
                645                 650                 655
Leu Lys Lys Ala Ile Phe Ser Pro Glu Leu Tyr Glu Asn Ile Ala Glu
            660                 665                 670
Trp Ile Val Ala His Trp Trp Ala Val Leu Leu Met Gly Ile Ala Leu
        675                 680                 685
Ile Met Leu Met Ala Gly Phe Ile Lys Ile Cys Ser Val His Thr Pro
        690                 695                 700
Ser Ser Asn Pro Lys Leu Pro Pro Pro Lys Pro Leu Pro Gly Thr Leu
705                 710                 715                 720
Lys Arg Arg Arg Pro Pro Gln Pro Ile Gln Gln Pro Gly Arg Gln Arg
                725                 730                 735
Pro Arg Glu Ser Tyr Gln Met Gly His Met Arg Arg
            740                 745
```

<210> SEQ ID NO 3
<211> LENGTH: 33
<212> TYPE: DNA
<213> ORGANISM: homo sapiens

<400> SEQUENCE: 3
tcaggggcca cttcccccat caaccctgcc gtg          33

<210> SEQ ID NO 4
<211> LENGTH: 11
<212> TYPE: PRT
<213> ORGANISM: homo sapiens

<400> SEQUENCE: 4

Ser Gly Ala Thr Ser Pro Ile Asn Pro Ala Val
1               5                   10

<210> SEQ ID NO 5
<211> LENGTH: 33
<212> TYPE: DNA
<213> ORGANISM: artificial sequence
<220> FEATURE:
<223> OTHER INFORMATION: human L1 mutant

<400> SEQUENCE: 5
tcaggggccg ctgcccccat caaccctgcc gtg          33

```
<210> SEQ ID NO 6
<211> LENGTH: 11
<212> TYPE: PRT
<213> ORGANISM: artificial sequence
<220> FEATURE:
<223> OTHER INFORMATION: human L1 mutant

<400> SEQUENCE: 6

Ser Gly Ala Ala Ala Pro Ile Asn Pro Ala Val
1               5                   10

<210> SEQ ID NO 7
<211> LENGTH: 6
<212> TYPE: PRT
<213> ORGANISM: homo sapiens

<400> SEQUENCE: 7

Thr Ser Pro Ile Asn Pro
1               5

<210> SEQ ID NO 8
<211> LENGTH: 6
<212> TYPE: PRT
<213> ORGANISM: artificial sequence
<220> FEATURE:
<223> OTHER INFORMATION: mutated SH3 binding site

<400> SEQUENCE: 8

Ala Ala Pro Ile Asn Pro
1               5
```